(12) United States Patent
Woudenberg et al.

(10) Patent No.: US 6,890,409 B2
(45) Date of Patent: May 10, 2005

(54) BUBBLE-FREE AND PRESSURE-GENERATING ELECTRODES FOR ELECTROPHORETIC AND ELECTROOSMOTIC DEVICES

(75) Inventors: Timothy M. Woudenberg, Moss Beach, CA (US); Zbigniew T. Bryning, Campbell, CA (US); Reid B. Kowallis, Burlingame, CA (US)

(73) Assignee: Applera Corporation, Foster City, CA (US)

( * ) Notice: Subject to any disclaimer, the term of this patent is extended or adjusted under 35 U.S.C. 154(b) by 479 days.

(21) Appl. No.: 09/938,947

(22) Filed: Aug. 24, 2001

(65) Prior Publication Data

US 2003/0075445 A1 Apr. 24, 2003

(51) Int. Cl.[7] ............................................. G01N 27/403
(52) U.S. Cl. ...................... 204/242; 204/278; 204/291; 204/600
(58) Field of Search ................................ 204/600, 601, 204/606, 242, 278, 291

(56) References Cited

U.S. PATENT DOCUMENTS

| | | | |
|---|---|---|---|
| 4,001,100 A | | 1/1977 | Haydock ................. 204/180 R |
| 4,351,709 A | * | 9/1982 | Goetz ......................... 204/549 |
| 5,035,790 A | * | 7/1991 | Morimoto et al. ..... 204/290.04 |

(Continued)

FOREIGN PATENT DOCUMENTS

| | | | |
|---|---|---|---|
| JP | 63302352 A | * 12/1988 | .......... G01N/27/26 |
| WO | WO 98/09161 | 3/1998 | |
| WO | WO 98/48084 | 10/1998 | |
| WO | WO 98/49549 | 11/1998 | |
| WO | WO 99/29711 | 6/1999 | |
| WO | WO 99/49319 | 9/1999 | |
| WO | WO 99/50480 | 10/1999 | |
| WO | WO 00/42424 | 7/2000 | |
| WO | WO 00/73780 A1 | 12/2000 | |
| WO | WO 00/74850 A2 | 12/2000 | |

OTHER PUBLICATIONS

Granger et al., Standard Electrochemical Behavior of High–Quality, Boron–Doped Polycrystalline Diamond Thin–Film Electrodes, Analytical Chemistry, vol. 72, No. 16, pp. 3793–3804 (Aug. 15, 2000).

(Continued)

Primary Examiner—Nam Nguyen
Assistant Examiner—Brian L. Mutschler
(74) Attorney, Agent, or Firm—Kilyk & Bowersox, P.L.L.C.

(57) ABSTRACT

Bubble-free electrodes, electrochemical cells including bubble-free electrodes, analytical devices, and methods for preparing and using them are provided. The analytical devices each include at least one bubble-free electrode. Analytical devices that include an electrochemical cell and a sample containment device are also provided, wherein the electrochemical cell includes an anodic reservoir, a cathodic reservoir, an electrical connection between the anodic reservoir and the cathodic reservoir, and a first bubble-free electrode disposed within one of the anodic reservoir and the cathodic reservoir. A second electrode is disposed within the other reservoir and a power source is provided having a positive terminal that is normally in electrical contact with the first electrode, and a negative terminal that is normally in electrical contact with the second electrode. The analytical device further includes a power source polarity-inverting device for switching the contacts between the terminals of the power source and the first and second electrodes. The sample containment device includes a sample containment chamber having an opening for introducing a sample into the chamber and being positioned with respect to the electrochemical cell such that an electrical field generated by the electrochemical cell can influence a property of a component of a sample disposed in the sample containment chamber. Pressure-generating cells are also provided.

14 Claims, 13 Drawing Sheets

U.S. PATENT DOCUMENTS

| | | | | |
|---|---|---|---|---|
| 5,240,576 | A | | 8/1993 | Lauer et al. ............. 204/180.1 |
| 5,540,831 | A | * | 7/1996 | Klein ........................ 205/630 |
| 5,605,662 | A | | 2/1997 | Heller et al. ............... 422/68.1 |
| 5,624,539 | A | * | 4/1997 | Ewing et al. ............... 204/451 |
| 5,632,957 | A | | 5/1997 | Heller et al. ............... 422/68.1 |
| 5,833,826 | A | | 11/1998 | Nordman .................... 204/452 |
| 5,858,187 | A | | 1/1999 | Ramsey et al. ............. 204/452 |
| 5,965,452 | A | | 10/1999 | Kovacs ....................... 436/149 |
| 6,001,229 | A | * | 12/1999 | Ramsey ...................... 204/451 |
| 6,045,676 | A | | 4/2000 | Mathies et al. ............. 204/603 |
| 6,068,818 | A | | 5/2000 | Ackley et al. ............... 422/50 |
| 6,071,394 | A | | 6/2000 | Cheng et al. ............... 204/547 |
| 6,077,625 | A | * | 6/2000 | Yano et al. ................. 429/223 |
| 6,099,803 | A | | 8/2000 | Ackley et al. ............. 422/68.1 |
| 6,102,897 | A | | 8/2000 | Lang |
| 6,103,199 | A | * | 8/2000 | Bjornson et al. ........... 422/100 |
| 6,129,828 | A | | 10/2000 | Sheldon, III et al. ....... 204/518 |
| 6,159,353 | A | | 12/2000 | West et al. ................. 204/601 |
| 6,174,675 | B1 | | 1/2001 | Chow et al. ................. 435/6 |
| 6,267,864 | B1 | | 7/2001 | Yadav et al. ................ 205/341 |
| 6,379,516 | B1 | * | 4/2002 | Cabilly et al. .............. 204/456 |
| 6,416,642 | B1 | | 7/2002 | Alajoki et al. .............. 204/451 |
| 6,458,259 | B1 | * | 10/2002 | Parce et al. ................. 204/454 |
| 6,471,841 | B1 | | 10/2002 | Nikiforov et al. .......... 204/454 |
| 6,476,539 | B1 | | 11/2002 | Takeuchi et al. ............ 310/330 |
| 6,569,306 | B1 | * | 5/2003 | Read et al. .................. 204/456 |
| 2002/0166592 | A1 | * | 11/2002 | Liu et al. .................... 137/825 |

OTHER PUBLICATIONS

Zak et al., *Diamond Optically Transparent Electrodes: Demonstration of Concept with Ferri/Ferrocyanide and Methyl Viologen, Analytical Chemistry*, vol. 73, No. 5, pp. 908–914 (Mar. 1, 2001).

Xu et al., *Boron–Doped Diamond Thin–Film Electrodes, Analytical Chemistry*, vol. 69, pp. 591A–597A (Oct. 1, 1997).

Washizu et al., *Molecular Dielectrophoresis of Biopolymers, IEEE Transactions on Industry Applications*, vol. 30, No. 4, pp. 835–843 (Jul./Aug. 1994).

Carrilho, *DNA Sequencing by Capillary Array Electrophoresis and Microfabricated Array Systems, Electrophoresis*, vol. 21. pp. 55–65 (2000).

Bruin, *Recent Developments on Electrokinetically Driven Analysis in Microfabricated Devices, Electrophoresis*, vol. 21, pp. 3931–3951 (2000).

Rocklin et al., *A Microfabricated Fluidic Device for Performing Two–Dimensional Liquid–Phase Separations, Analytical Chemistry*, vol. 72, No.21, pp. 5244–5249 (Nov. 1, 2000).

Krishnamoorthy et al., *Analysis of Sample Injection and Band–Broadening in Capillary Electrophoresis Microchips, Modeling and Simulation of Microsystems*, Applied Computational Research Society, vol. 3 (2000).

Becker et al., *Polymer Microfabrication Methods for Microfluidic Analytical Applications, Electrophoresis*; vol. 21, pp. 12–26 (2000).

Dolnik et al., *Capillary Electrophoresis on Microchip, Electrophoresis*, vol. 21, pp. 41–54 (2000).

Huang et al., *Electric Manipulation of Bioparticles and Macromolecules on Microfabricated Electrodes, Analytical Chemistry*, vol. 73, No. 7, pp. 1549–1559 (Apr. 1, 2001).

Liu et al., *Optimization of High–Speed DNA Sequencing on Microfabricated Capillary Electrophoresis Channels, Analytical Chemistry*, vol. 71, No. 3, pp. 566–573 (Feb. 1, 1999).

McDonald et al., *Fabrication of Microfluidic Systems in Poly(dimethylsiloxane), Electrophoresis*, vol. 21, pp. 27–40 (2000).

Morgan et al., *Separation of Submicron Bioparticles by Dielectrophoresis, Biophysical Journal*, vol. 77, pp. 516–525 (Jul. 1999).

García Campaña et al., *Miniaturization of Capillary Electrophoresis Systems Using Micromachining Techniques, Journal of Microcolumn Separation*, vol. 10, No. 4, pp. 339–355 (1998).

Simpson et al., *A Transmission Imaging Spectrograph and Microfabricated Channel System for DNA Analysis, Electrophoresis*, vol. 21, pp. 135–149 (2000).

Alien Technology document or printout for 185 and 70 Micron NanoBlock circuits on top of a dime, and flexible PET substrate, one page (not dated).

Nanogen document or printout for NanoChip Molecular Biology Workstation, one page, showing workstation with enlargement of 99–site test array (not dated).

Copy of International Search Report from PCT/US02/26657 dated Dec. 9, 2002.

* cited by examiner

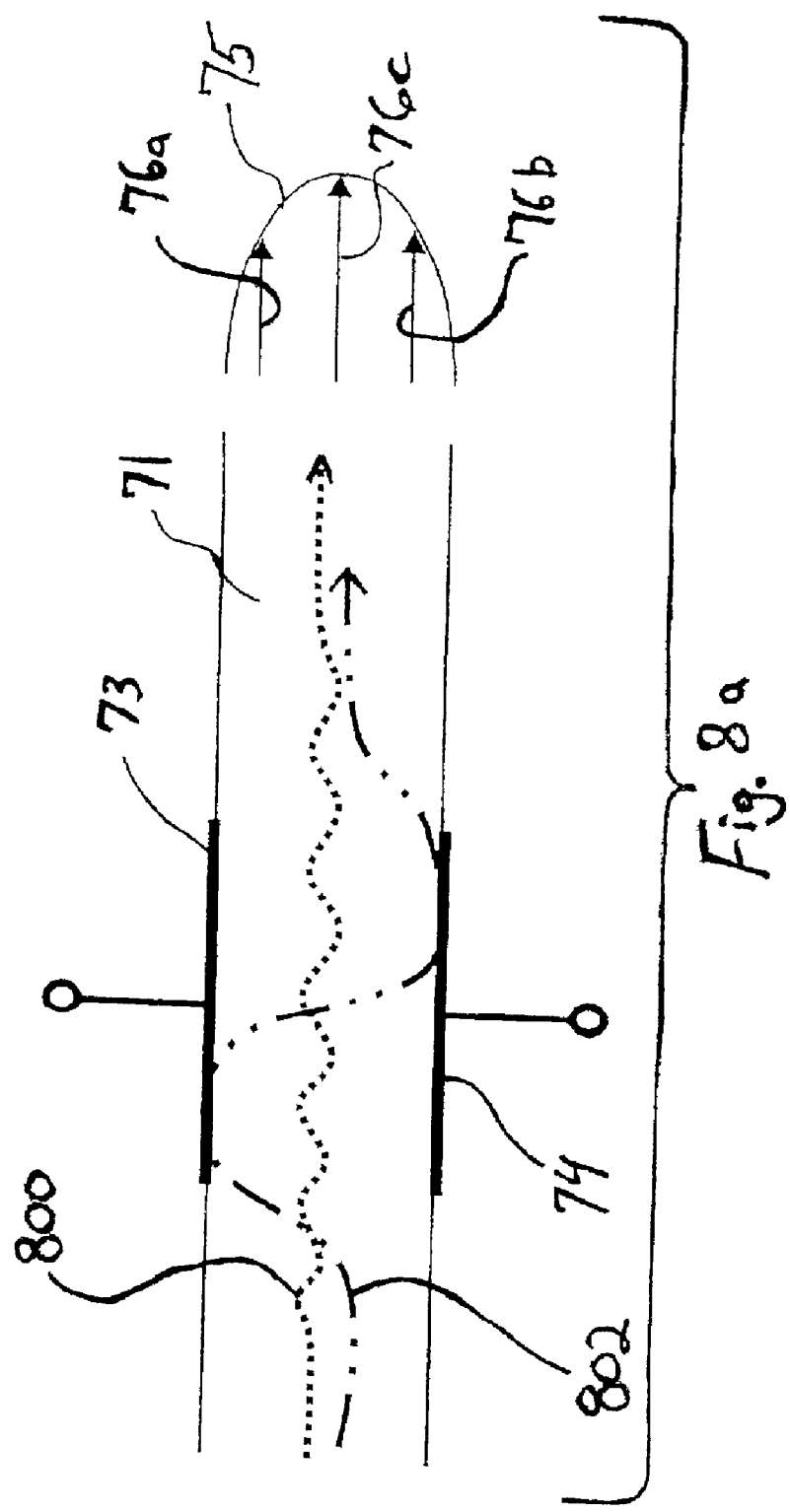

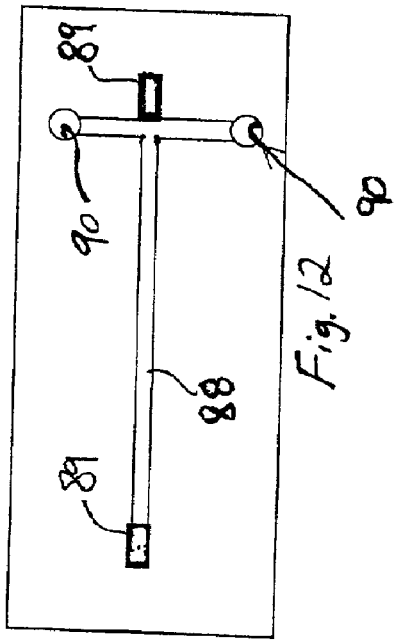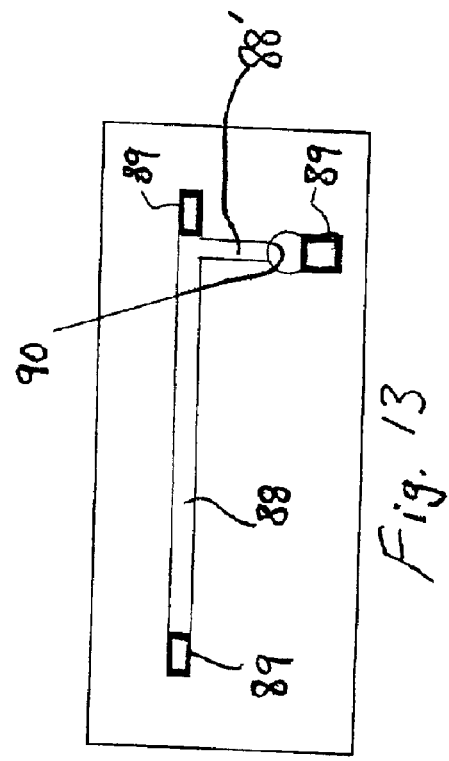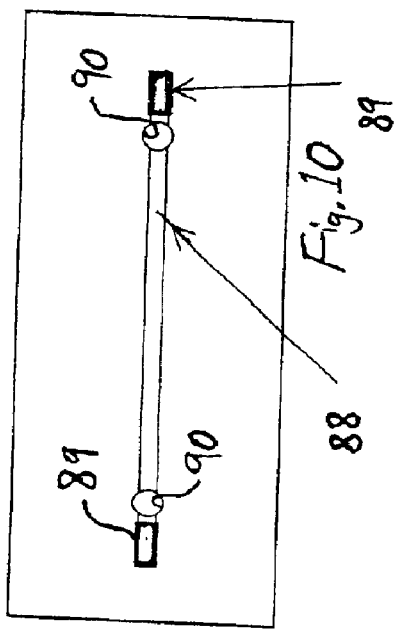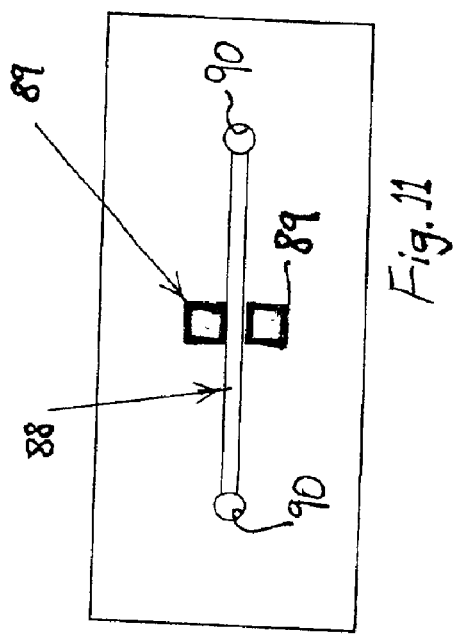

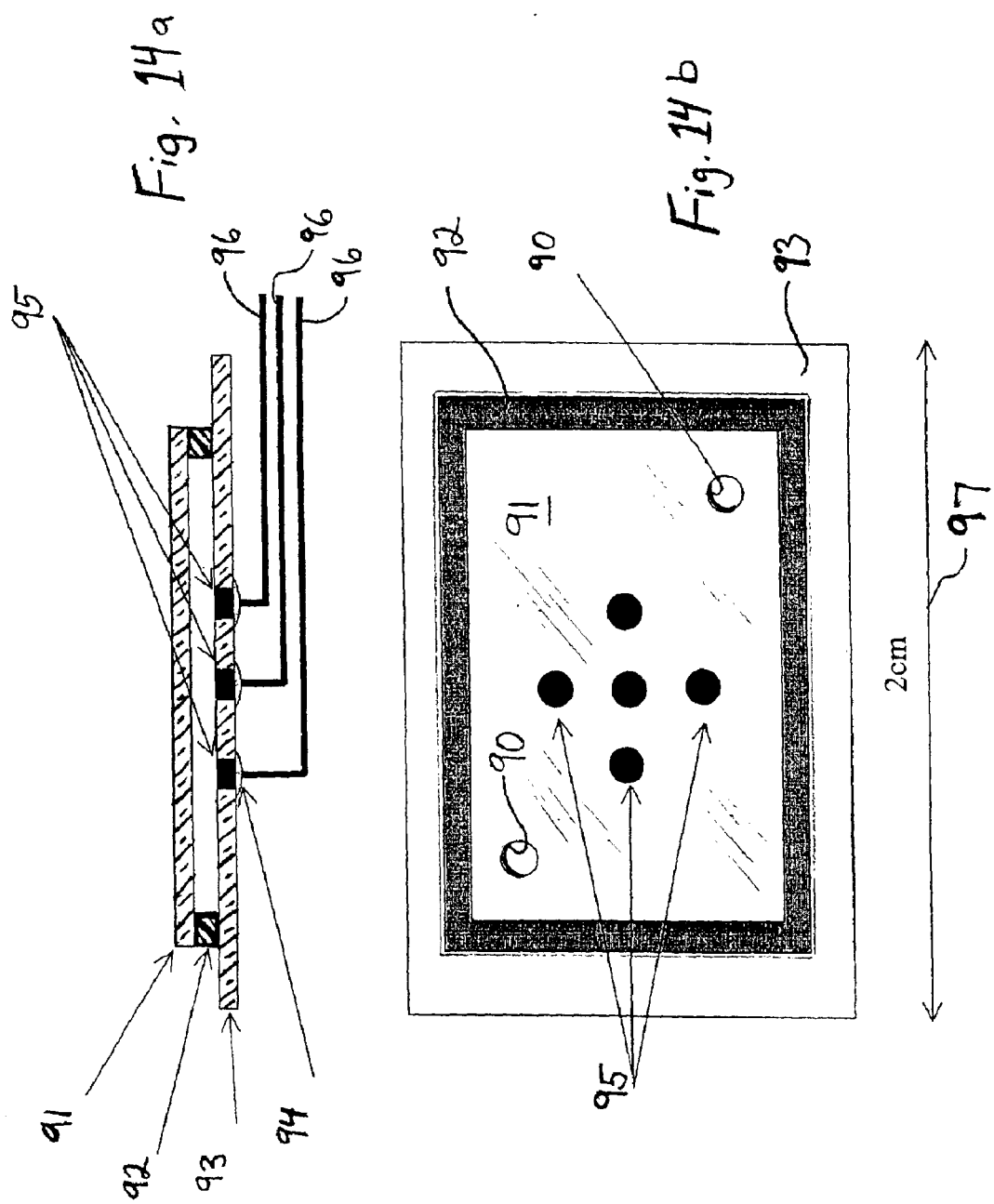

BUBBLE-FREE AND PRESSURE-GENERATING ELECTRODES FOR ELECTROPHORETIC AND ELECTROOSMOTIC DEVICES

BACKGROUND OF THE INVENTION

For many applications regarding the generation of an electric field in an aqueous medium, electrodes are typically placed directly in an aqueous buffer solution and connected to an external power source to form an applied voltage difference. If the applied voltage exceeds about one volt, as is typical in electrophoretic and electroosmotic applications, the applied voltage causes electrolysis of water. The electrolysis results in the generation of hydrogen gas at the cathode (negative electrode) and oxygen gas at the anode (positive electrode).

Problems exist in operating microchannel devices and other integrated devices for sequencing or concentrating biomolecules because of the need for a connection to an external source of current, usually a high-voltage power supply. Conventionally, such connections are made by dipping a wire, such as a platinum wire, in small containers filled with an electrolyte buffer solution. Generated hydrogen gas bubbles and oxygen gas bubbles resulting from electrolysis are vented or escape to the atmosphere.

In many devices that include an electrochemical cell, the formation of bubbles at one or both electrode surfaces can create serious problems. These devices include microbiological analytical devices, microelectrophoretic devices, bulk flow transport systems, and devices where electrodes must be placed in confined or sealed fluidic channels. Interfacing of such devices with the electrodes creates particular problems. Among these problems are siphoning, evaporation of electrolyte, excessive current path lengths and associated heating requirements, excessively complex electromechanical systems and configurations, excessively large systems and electrolyte reservoirs, excessive reagent and/or electrolyte consumption, and in some cases the impossibility of placing electrodes driven by DC or low frequency AC current inside channels or closed chambers.

Palladium has been used as an electrode material in electrophoretic devices, for example, the electrophoretic devices described in U.S. Pat. No. 5,833,826, which is incorporated herein in its entirety by reference. In addition, it is well known that palladium absorbs hydrogen. However, palladium does not absorb oxygen gas generated at the positive electrode of an electrochemical cell rendering it undesirable as an electrode material in microbiological analytical devices, microelectrophoretic devices, bulk flow transport systems, and devices where electrodes must be placed in confined or sealed fluidic channels.

SUMMARY OF THE INVENTION

The present invention overcomes problems associated with electrodes that produce bubbles by providing a bubble-free electrode material and systems and methods employing its use. The devices of the present invention include one or more bubble-free electrodes, methods of preparing bubble-free electrodes, and analytical methods that employ devices including bubble-free electrodes. Herein, the phrase "bubble-free electrode" encompasses different electrodes that produce no bubbles during operation as defined herein.

According to an embodiment of the present invention, bubble-free palladium electrodes prepared according to the invention are provided that produce less bubbles than similarly dimensioned palladium electrodes not prepared according to the invention under similar environmental and electrical conditions.

According to an embodiment of the present invention, bubble-free palladium electrodes prepared according to the invention are provided that produce less bubbles than similarly dimensioned platinum electrodes not prepared according to the invention under similar environmental and electrical conditions.

According to yet another embodiment of the present invention, bubble-free anodes are provided that do not generate an oxygen bubble visible to the naked eye when charged at a current density of about 72 $A/m^2$ (amperes per square meter) for about 1.0 second in a degassed electrolytic solution under conditions of ready-nucleation, that is, under conditions where spontaneous bubble formation prevents supersaturation of dissolved oxygen.

According to yet another embodiment of the present invention, a palladium anode is provided that includes hydrogen stored in the anode material in an amount sufficient to reduce the formation of oxygen gas bubbles by the anode under electrolytic conditions when compared to a comparably dimensioned palladium electrode not including the stored hydrogen.

According to an embodiment of the present invention, an electrochemical cell is provided that includes one or more palladium anodes that has been pre-charged as a cathode to absorb and store hydrogen within the electrode structure. Subsequently the electrode is used as an anode under electrolytic conditions to operate bubble-free. In an exemplary embodiment of the present, an electrochemical cell is provided that includes a palladium-containing electrode that operates as an anode under normal operation of the cell, but that has been pre-charged under conditions as a cathode. During pre-charging, hydrogen generated at the cathode is absorbed and stored in the structure of the cathode. When the electrode is charged under reverse-electrical polarity conditions, the palladium metal material absorbs and accumulates hydrogen. After an amount of time has elapsed under the respective reversed electrical conditions, a sufficient amount of hydrogen is absorbed to enable the electrode to operate under normal operation as a bubble-free anode. The electrode can be pre-charged for a predetermined time under the respective electrical conditions such that under subsequent normal operating conditions, the electrode operates as a bubble-free anode.

The present invention also provides electrochemical cells that include other hydrogen-absorbing materials as cell electrode materials, particularly as materials for electrodes that normally operate as anodes under normal operation of the cell. To accomplish storage of hydrogen in palladium and other hydrogen-absorbing materials, an electrode of the material can be run under cathodic conditions prior to being used as an anode. An electrochemical cell including a switch is provided according to an embodiment of the present invention whereby the polarity of the electrochemical cell can be reversed to enable the cell to run under reverse or pre-charging operation.

Whether a switch is provided or the cell is otherwise temporarily caused to operate under pre-charging conditions of reverse polarity, pre-charging can be accomplished to an extent or for an amount of time sufficient to enable the electrode to then operate under anodic conditions as a bubble-free electrode.

According to an embodiment of the present invention, a device for affecting one or more properties of a component in a sample is provided that includes a bubble-free electrode. The device can include a palladium electrode as the bubble-free electrode, or some other electrode material or combination of materials.

Methods of generating an electrical field with one or more of the anodes and bubble-free electrodes of the present invention are also provided as are methods of separating components in a sample by exposing the components to a field generated by one or more anodes or bubble-free electrodes of the present invention.

According to embodiments of the present invention, methods are also provided wherein an electrochemical cell including a bubble-free electrode is used to generate a field in a device, wherein the field is useful to affect one or more properties of a component of a sample. For example, devices are provided according to the present invention wherein a bubble-free electrode is employed to generate a field that is used to affect the mobility of one or more components of a sample, for instance, to cause separation of sample components.

Other embodiments of the present invention include microchip devices including pressure generators configured with frangible or meltable seals and electronics to accomplish precise sample injection and separation of nanoliter-sized samples.

All patents and publications mentioned herein are incorporated herein in their entireties by reference.

It is to be understood that both the foregoing general description and the following detailed description are exemplary and explanatory only and are only intended to provide a further explanation of the present invention, as claimed. The accompanying drawings, which are incorporated in and constitute a part of this application, illustrate several exemplary embodiments of the present invention, and, together with description, serve to explain the principles of the present invention.

BRIEF DESCRIPTION OF THE DRAWINGS

The present invention may be more fully understood with reference to the accompanying figures. The figures are intended to illustrate exemplary embodiments of the present invention without limiting the scope of the invention.

FIG. 2a is a top view of an analytical device according to an embodiment of the present invention;

FIG. 2b is a cross-sectional view taken along line IIb of FIG. 2a;

FIG. 7b is a top view of a sealing device for sealing the ends of a plurality of capillary tubes, such as the tubes depicted in FIG. 7a;

FIG. 8a is a side view of a low frequency concentrator according to an embodiment of the present invention using a pressure driven flow profile to affect separation of components in a sample;

FIGS. 10-13 are top views of various exemplary analytical devices according to embodiments of the present invention;

FIGS. 14a and 14b are a side view and top view, respectively, of an analytical device according to yet another embodiment of the present invention;

DETAILED DESCRIPTION OF THE PRESENT INVENTION

Figure 1:
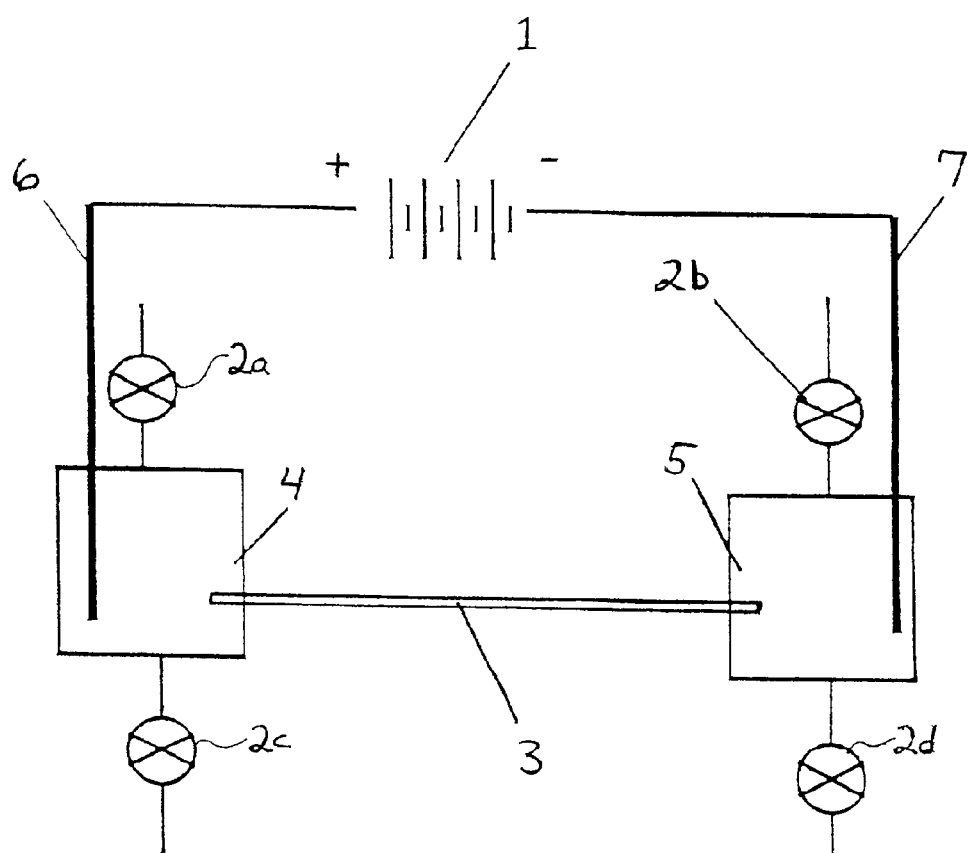
FIG. 1 is a schematic view of an example of an analytical device according to an embodiment of the present invention.

The bubble-free electrodes of the present invention can include a variety of designs and compositions. Different materials and designs can be used to obtain the bubble-free electrodes of the present invention, including different chemical compounds and combinations of compounds. An example of a bubble-free electrode useful in accordance with the present invention is a palladium metal anode.

Palladium metal anodes are particularly useful in accordance with an embodiment of the present invention. When palladium is used as a cathode under conditions that result in the electrolysis of water, the palladium is able to store hydrogen generated by the cathode by absorbing the hydrogen in the interstices of the palladium lattice. In metal electrodes that do not include palladium, hydrogen is not absorbed by the metal but rather leads to the production of hydrogen gas bubbles at the electrode surface. According to embodiments of the present invention, palladium anodes are provided that include stored hydrogen useful in preventing the formation of oxygen bubbles at the anode during operation of a cell including the anode.

The capacity to store hydrogen is strongly influenced by the temperature of the anode, the rate at which hydrogen is generated, the morphology of the palladium surface, and the crystal grain size of the palladium. Guidance for enabling those skilled in the art to optimize parameters and resulting electrode characteristics is provided by the exemplary electrodes, devices, and Examples set forth herein. Once the hydrogen-storing capacity is exceeded, the palladium anode will generate hydrogen bubbles unless something is done to deplete the electrode of stored hydrogen. The anode can be prepared with hydrogen by reversing the polarity in this same step to render it a cathode, and simultaneously the cathode can be run as an anode and depleted of hydrogen in preparation for the next cycle.

According to embodiments of the present invention wherein an electrochemical cell is provided and the cell anode is pre-charged under reverse polarity conditions to store hydrogen, the amount of time for operating the electrode under pre-charging conditions can depend upon the current and voltage provided by the power supply. A sufficient amount of pre-charging time can be an amount of time under which the anode attains at least about 1% or greater of its hydrogen absorption capacity, for example, greater than 50% of its hydrogen absorption capacity, greater than 90% of its hydrogen absorption capacity, or to about the full hydrogen absorption and storage capacity of the electrode.

Although the palladium metal material and other electrode materials used according to an embodiment of the present invention may not store oxygen gas, when a cell including the material is operated under normal anodic operating conditions following pre-charging, the formation of oxygen gas bubbles at or due to the electrode are prevented or reduced. Instead of generating oxygen gas, the pre-charged palladium or hydrogen-absorbing electrode, for example anode, of the present invention reacts with the reservoir of hydrogen stored in the pre-charged electrode material. As a result of pre-charging, the stored hydrogen is oxidized rather than generating oxygen gas.

According to an exemplary embodiment of a method and device according to the present invention, a first electrode, which operates as an anode under normal operating conditions, operates as an cathode during a reverse-polarity pre-charging preparation process. The first electrode can be pre-charged ex-situ, or pre-charged in-situ. When pre-charged in-situ, a device including the electrode can be operated under open or pre-sealed conditions so that bubbles generated by the electrode operating as an anode during pre-charging can be vented to the atmosphere while hydrogen accumulates at the hydrogen-absorbing electrode acting as a cathode during pre-charging. After a pre-charging period of sufficient length to enable the electrode to store an adequate amount of hydrogen under the respective electrical conditions, the cell can be sealed.

The cell can be pre-charged and then sealed or closed prior to normal operation or during normal operation. Electrolysis can be discontinued during sealing or closing the cell and the cell can subsequently operate under normal conditions as a bubble-free electrode for a period of time. According to an embodiment of the present invention, the sealed or closed cell can operate after pre-charging under conditions such that an electrode, previously pre-charged to store hydrogen, operates as a bubble-free anode.

The cell can be pre-charged while simultaneously venting oxygen gas produced during the pre-charging process. After the preparation and venting, the device can be permanently sealed without the need to vent again.

According to embodiments of the present invention, a device can be created that includes an electrochemical cell that can operate bubble-free under normal electrolytic operation for extended periods of time limited mainly by the volume of hydrogen stored at the electrode and the ability of the cell to prevent oxygen bubble formation at the cell anode. According to embodiments of the present invention, a device such as that shown in FIG. 9, having, for example, a 10 cm separation channel, is provided that includes an electrochemical cell that can operate bubble-free under normal electrolytic operation (i.e., under normal polarity, not reverse polarity, conditions) for at least about 20 minutes at a current of up to about 5 mA and a voltage of up to about 2 kV (kilovolts).

According to an embodiment of the present invention, a bubble-free anode electrode is provided that does not generate an oxygen bubble at the anode if the current density is held at 72 A/m$^2$ (amperes per square meter) for one second. This assumes that the solution has been previously degassed and that bubble formation is readily nucleated. In determining a condition for bubble-free operation according to an embodiment of the present invention, an electrolysis of pure distilled water on the surface of an infinite plane electrode was tested at standard conditions including a temperature of 25° C. and a pressure of 1 atm. It was assumed that as a result of the electrolysis, oxygen bubbles would be created on the electrode surface when the oxygen concentration on that surface reaches a saturation value $C_s$. How quickly this happens depends on the electric current density j at which this electrode operates and on initial oxygen concentration $C_0$ dissolved in the water. It was also assumed that oxygen is transported away from the electrode only by means of diffusion, and the oxygen diffusion coefficient is D. The time For the oxygen concentration to reach the saturation value at the surface of the electrode is given by the following formula:

$$t=64\times pF^2(C_s-C_o)\times D/j^2 \tag{1}$$

where F is Faraday's constant and equals=96500 C/mol. Formula (1) allows estimations for critical time as a function of initial oxygen concentration and current density. For oxygen $C_s$=1.3 mM/L and D=2×10$^{-5}$ cm$^2$/s at T=25° C. Assuming that initial oxygen concentration is 0.1×$C_s$, one can calculate that t=5120/j$^2$. Thus, t=1 second if j=72 A/m$^2$. As a reference, the current density in a 50 mm capillary at a current of 10 mA is about 5000 A/m$^2$.

An electrochemical cell is also provided according to the present invention that includes a bubble-free palladium anode of such specifications. A sample separation device including such an electrode is also provided by the present invention as is an electrophoretic device including such a palladium anode.

According to an embodiment of the present invention, a device for affecting one or more properties of a component in a sample is provided that includes a bubble-free electrode. The device can include a palladium electrode as the bubble-free electrode, or some other electrode material or combination of materials. An exemplary embodiment is a device including an electrochemical cell having an electrode system that includes Mg$_2$Ni, (RE)Ni$_5$ wherein RE is a rare earth element, LiNiO$_2$, V$_2$O$_5$, or mixtures, combinations, or combined uses thereof. Other bubble-free cells and systems that can be used according to embodiments of the present invention to form a field that affects a property of a sample component include reversible electrodes such as those described in U.S. Pat. No. 5,605,662, galvanic cells, RAM cells, nickel-cadmium cells, AC voltage-powered electrodes, microfabricated cells and devices, and other bubble-free cells and electrode systems, and combinations thereof.

According to embodiments of the present invention, an electrochemical cell is provided that can operate bubble-free under voltage conditions of at least about 3 volts, for example, at least about 5 volts. According to embodiments of the present invention, an electrochemical cell is provided that can operate bubble-free under voltage per length conditions of at least about 10 volts/cm, for example, at least about 25 volts/cm. According to embodiments of the present invention, an electrochemical cell is provided that can operate bubble-free under voltage per length conditions of up to about 100 volts/cm. According to embodiments of the present invention, an electrochemical cell is provided that can operate bubble-free under voltage conditions of up to about 200 volts/cm. For electrochemical cells according to the present invention including hydrogen-absorbing electrodes, the cells can operate bubble-free under these electrical conditions while under electrolytic conditions.

According to an embodiment of the present invention, a device for affecting one or more properties of a component in a sample is provided that includes a bubble-free electrode material other than palladium. An exemplary embodiment is a device including an electrochemical cell having an electrode system that includes $Mg_2Ni$, $(RE)Ni_5$ wherein RE is a rare earth element, $LiNiO_2$, $V_2O_5$, or mixtures, combinations, or combined uses thereof.

Other bubble-free electrode materials and systems that can be used according to embodiments of the present invention include RAM cells such as $MnO_2$, $MnOOH|H_2O$, $KOH|Zn$, $ZnO$, nickel-cadmium cells such as $Cd$, $CdO|KOH(20\% \text{ aqueous})|Ni(OH)_4$, $Ni(OH)_2$, $Ni$, and others.

According to embodiments of the present invention, electrode materials for bubble-free electrode operation in devices and methods of the present invention include electroplated iridium oxide electrodes.

According to embodiments of the present invention, electrode materials for bubble-free electrode operation in devices and methods of the present invention include ionic conductors, polymer electrolytes, liquid electrolytes, gels, polyethylene oxide (PEO) materials, ceramics such as NASICON, NAFION membranes, and the like, and mixtures and combinations thereof. The present invention also encompasses combinations of two or more of these electrode materials as bubble-free electrode materials. An example of such a combined material is a mixture of $Ni(OH)_x$ electrode material with NAFION, PEO materials, gels such as polyacrylamides and gelatin, cross-linked gels, ionic liquid electrolytes such as organic molten salts, or polymer electrolytes. Electrodes can be made from such mixed materials or such materials can be used as, for instance, covering materials for electrodes as described in U.S. Pat. Nos. 6,245,508; 6,129,828; and 5,849,486, which are herein incorporated in their entireties by reference. Other electrode or electrolytic materials useful according to embodiments of the present invention include ionic liquids, for example, those that behave electronically like salt melts. Exemplary useful liquids according to an embodiment of the present invention remain fluid over a temperature range of about 300° C., and/or have very low vapor pressure. Imidazole-based ionic liquids can be used, including those having the formula:

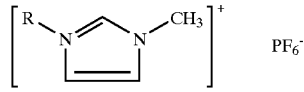

wherein R is a lower alkyl group of 20 carbon atoms or less, a methyl group, an ethyl group, a propyl group, a butyl group, or other organic groups containing about 20 or fewer carbon atoms. The ionic liquid can be a salt with $PF_6^-$ as shown, or a salt with another anion.

In addition, other electrode materials and designs that can be used in accordance with embodiments of the present invention include those electrodes and designs taught in concurrently filed U.S. patent application Ser. No. 09/938,894, to Bryning et al., entitled "Manipulation of Analytes Using Electric Fields", which is incorporated herein in its entirety by reference.

Finely divided palladium and porous palladium are useful bubble-free electrode materials. Methods of manufacturing using these materials can provide a wide range of advantages. By applying a paste to a substrate and annealing at temperatures of up to 800° C. or higher, or by just drying the electrodes, the electrodes can be made on various substrates including metals, glasses, plastics, and the like, depending on the desired application.

Bubble-free electrodes according to embodiments of the present invention can be chemically stable at a pH of from about 7 to about 9, for example, at a pH of about 8. Preferably, the electrodes exhibit low toxicity and are easily formed.

According to embodiments of the present invention, an analytical device is provided that includes an electrochemical cell and a sample containment device. The electrochemical cell includes at least an anodic reservoir, a cathodic reservoir, an electrical connection between the anodic reservoir and the cathodic reservoir, and at least a first bubble-free electrode disposed within one of the anodic reservoir and the cathodic reservoir. A second electrode is disposed within the other reservoir and may also be a bubble-free electrode. A power source is provided having a more positive terminal that is normally in electrical contact with the first electrode, and a more negative terminal that is normally in electrical contact with the second electrode. The electrochemical cell operates in an electrolytic mode and generates an electrical field when the power source is turned on and the cell is operating in a normal mode of operation. The analytical device further includes a power source polarity-inverting device for switching the contacts between the terminals of the power source and the first and second electrodes.

By reversing the polarity of the terminals, the cell can be reverse-charged such that one or more of the electrodes stores or creates a bubble-preventing compound that prevents formation of bubbles at the electrode surface when the cell is run in the normal electrolytic mode of operation. The sample containment device includes a sample containment chamber having an opening for introducing a sample into the chamber. The opening can be positioned with respect to the electrochemical cell such that an electrical field generated by the electrochemical cell can influence at least one property, such as mobility, of at least one component of a sample disposed in the sample containment chamber.

Because the bubble-free electrodes of the present invention can be embodied in self-contained devices such as card-type devices already preloaded with reagents and separation medium, they are particularly useful in integrated disposable devices. More particularly, the bubble-free electrodes of the present invention can be embodied in sealed devices such as card-type devices already preloaded with reagents and separation medium, sealed to prevent evaporation, and containing only, for example, a sample entrance port, where they are particularly useful in integrated disposable devices. The present invention also enables low-voltage bubble-free electrodes useful for capturing and moving biomolecules. Another application of the present invention is in the form of inexpensive, disposable, washable, or refreshable devices used in high-throughput laboratories for sample preparation, sample concentration, sample purification, sample delivery, and in separation devices and methods.

Another use according to the present invention is to concentrate negatively charged biomolecules or dye molecules on an electrode and enable plug release into a channel whereby a plug of concentrated biomolecules can be released into a channel as a single plug or pulse. Another use is to demonstrate concentration and manipulation of negatively charged dyes in array-like formats as electrodes on planar surfaces. Further examples of such devices are described in more detail below, such as the devices shown in, and described in connection with, FIGS. 10, 11, 12, 14, and 15.

According to yet another embodiment of the present invention, an analytical device is provided that includes a flow pathway, a flow manipulating cell adjacent the flow pathway, and a pressure relief pathway. The flow manipulating cell includes a confined reservoir, an exit port in communication with the reservoir, and a pressure generating electrode in the reservoir. The pressure generating electrode generates gas bubbles within the reservoir upon application of a controlled power source for increasing pressure within the cell. The pressure relief pathway is in communication with the flow pathway and is useful for affecting a flow through the flow pathway. The pressure-generating electrode can be a palladium electrode, for example, a bubble-free palladium anode of the present invention. The pressure-generating electrode can be a palladium anode that runs bubble-free for a time period of at least one second when held at a current density of about 72 $A/m^2$ in a previously degassed solution. The flow pathway can include an electrophoretic separation channel. The exit port can include a frangible seal, for example, a heat-meltable seal that is in communication with a heating element.

The present invention also provides methods of forming bubble-free electrodes and electrochemical cells, and analytical devices containing the same, methods of manipulating components of a sample in an electric field formed by one or more of the electrodes and/or cells of the present invention, and methods of sample injection using a pressure-generating electrode according to the present invention. In addition, the present invention relates to the use of bubble-free electrodes in sample preparation and clean-up applications, in detection applications such as described in U.S. Pat. No. 5,833,826, herein referred to as "electroflow" applications, in active programmable electronics devices, in Alien Technology nanoblock circuit technology, in the devices described in U.S. Pat. No. 6,071,394, in self-contained card devices for diagnostics applications, in sample preparation methods, in traveling wave separation methods, in multi-step separation methods, in synchronized cyclic capillary electrophoresis methods, and the like.

Exemplary devices, systems, and methods which can be adapted according to the present invention to employ the bubble-free electrodes and methods of using same according to the present invention include those described in U.S. Pat. No. 6,129,828; U.S. Pat. No. 6,099,803; U.S. Pat. No. 6,071,394; U.S. Pat. No. 6,068,818; U.S. Pat. No. 5,965,452; U.S. Pat. No. 5,833,826; U.S. Pat. No. 5,632,957; U.S. Pat. No. 5,605,662; U.S. Pat. No. 5,384,024; U.S. Pat. No. 5,240,576; U.S. Pat. No. 4,001,100; International Patent Publication No. WO 00/74850 A2; International Patent Publication No. WO 99/50480; International Patent Publication No. WO 99/14368; and International Patent Publication No. WO 98/48084, all of which are incorporated herein in their entireties by reference.

The bubble-free electrodes of the present invention, methods using them, and systems employing them, can be used in a wide variety of devices that include one or more electrodes. For example, various embodiments of the present invention can be utilized in the capillary electrophoresis microchips described by Krishnamoorthy et al. in the publication *Analysis of Sample Injection and Band-Broadening in Capillary Electrophoresis Microchips*, from CFD Research Corporation of Huntsville Ala.; in the microfluidic analytical devices described by Becker et al. in the publication *Polymer microfabrication methods for microfluidic analytical applications, Electrophoresis*, vol. 21, pp. 12–26 (2000); in the capillary electrophoresis microchips described by Dolnik et al. in the publication *Capillary electrophoresis on microchip, Electrophoresis*, vol. 21, pp. 41–54 (2000); in the microfabricated devices described by Huang et al. in the publication *Electric Manipulation of Bioparticles and Macromolecules on Microfabricated Electrodes, Analytical Chemistry*, vol. 2001, pp. 1549–1559 (2001); in the micromachining techniques and devices described by Campaña et al. in the publication *Microfabrication of Capillary Electrophoresis Systems Using Micromachining Techniques, J. Micro. Sep.* 10, pages 339–355 (1998); in the microfabricated capillary electrophoresis channels described by Liu et al. in the publication *Optimization of High-Speed DNA Sequencing on Microfabricated Capillary Electrophoresis Channels, Analytical Chemistry*, vol. 71, pp. 566–573 (1999); in the microfluidic systems described by McDonald et al. in the publication *Fabrication of microfluidic systems in poly(dimethylsiloxane), Electrophoresis*, vol. 21, pp. 27–40 (2000); in the dielectrophoresis submicron bioparticle separation devices and methods described by Morgan et al. in the publication *Separation of Submicron Bioparticles by Dielectrophoresis, Biophysical Journal*, vol. 77, pp. 516–525 (1999); in DNA molecule transportation described by Morishima et al. in the publication *Tranportation of DNA Molecule Utilizing the Conformational Transition in the higher order structure of DNA, CCAB* 97 published on the internet on Feb. 13, 1998; in the transmission imaging spectrographic and microfabricated channel systems described by Simpson et al. in the publication *A transmission imaging spectrograph and microfabricated channel system for DNA analysis, Electrophoresis*, vol. 21, pp 135–149 (2000); in the devices described by Soane et al. in U.S. Pat. No. 5,126,022; in the microchip electrodynamic focusing device and methods described by Ramsey et al. in U.S. Pat. No. 5,858,187; in the electrochemical detectors described by Mathies et al. in U.S. Pat. No. 6,045,676; in the capillary electrophoretic separation systems described by West et al. in U.S. Pat. No. 6,159,363; in the microfabricated devices described by Chow et al in U.S. Pat. No. 6,174,675 B1; in the microfabricated devices described by Simpson et al. in U.S. Pat. No. 6,236,945 B1; in the microchip devices described by Waters et al. in *Microchip Device for Cell Lysis, Multiplex PCR Amplification, and Electrophoretic Sizing, Analytical Chemistry*, vol. 70, pp. 158–162 (1998); in the biological detection systems described by Cheng et al. in PCT International Publication Number WO 00/37163; in the microfabricated capillary electrophoresis chip described by Mathies et al. in PCT International Publication Number WO 00/42424; in the microfabrication devices described by Bukshpan in PCT International Publication Number WO 00/73780 A1; in the microlithographic arrays described in PCT International Publication Number WO 94/29707; in the sorting devices described by Austin in PCT International Publication Number WO 98/0893; in the electrophoresis chips described by Mathies et al. in PCT International Publication Number WO 98/09161; in the capillary electrophoretic separation systems described by West et al. in PCT International Publication Number WO 98/49549; in the microfabrication devices described by Sosnovski et al. in PCT International Publication Number WO 99/29711; in the microfabrication devices described by Ostergaard et al. in PCT International Publication Number WO 99/49319; in the microfabricated capillary array electrophoresis chips described by Woolley et al. in *Ultra-high speed DNA frag-* ment separations using microfabricated capillary array electrophoresis chips, *Proceedings of the National Academy of Sciences*, USA vol. 91, pp. 11348–11352 (1994); in the microfabricated devices described by Woolley et al. in *Functional Integration of PCR Amplification and Capillary Electrophoresis in a Microfabricated DNA Analysis Device, Analytical Chemistry*, vol. 68, pp. 4081–4086 (1996); and in the capillary electrophoresis chips described by Woolley et al. in *Capillary Electrophoresis Chips with Integrated Electrochemical Detection, Analytical Chemistry*, vol. 70, pp. 684–688 (1998). All of these patents and other publications are incorporated herein in their entireties by reference.

Referring now to the drawing FIGS., in the embodiment of the present invention shown in FIG. 1, palladium electrode 6 and palladium electrode 7 are connected to a DC voltage source 1 and placed in closed reservoirs 4 and 5, respectively. The electrode 6 operates as an anode and the electrode 7 operates as a cathode under normal operating conditions. The normally-operating anode 6 is pre-charged, for example, prior to insertion into reservoir 4, or in-situ by reversing the charge on the electrode for a pre-charging period prior to normal operation. Pre-charging of the anode can be affected by exposure of the electrode to a hydrogen-rich environment.

Four valves 2a–2d are used to fill the reservoirs 4 and 5 with reagent. A capillary tube 3 is inserted into the two reservoirs 4 and 5 and filled with reagent. Because of the pre-charging of anode 6, the system produces no gas bubbles at anode 6 or at cathode under normal operating electrolytic conditions. Because no gas bubbles are generated during normal operation of the system, the reservoirs and capillary are able to be a closed system. Such a closed system is highly tolerant of differences in elevations of the two reservoirs since siphoning is prevented by the closed system.

An appropriate sample-filling feature such as one of those known to those skilled in the art, can be incorporated into the system. Depending upon factors including the charge of the components to be separated from a sample, sample injection can be configured at or near an appropriate end of capillary tube 3.

Figure 2:
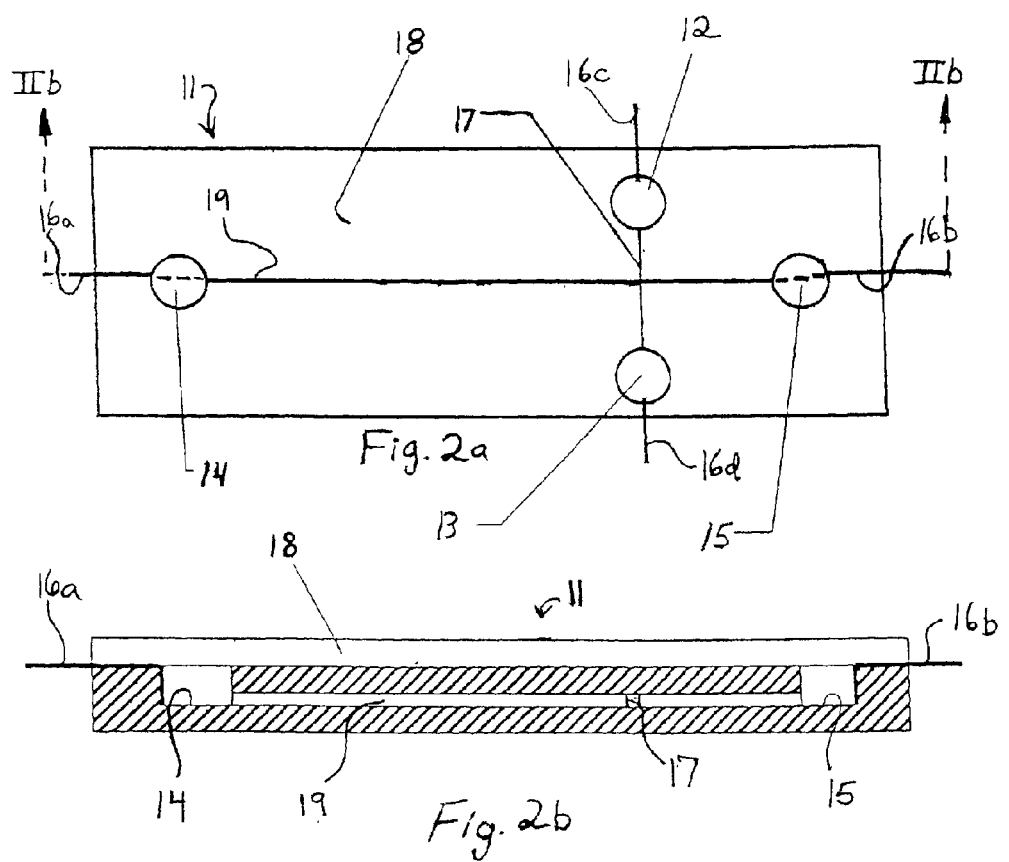

In an embodiment of the present invention such as shown in FIGS. 2a and 2b, the system is configured as a microfabricated device 11 including a T-injection feature. The device includes four electrodes 16a–16d, at least one of which includes a bubble-free electrode of the present invention. Any suitable leads can be provided for the electrodes 16a–16d, for example, protruding leads as shown. The device shown in FIGS. 2a and 2b can include, for example, four palladium material-containing electrodes. The electrodes are patterned into wells 12, 13, 14, and 15. A channel 19 is provided between patterned wells 14 and 15, along which electrophoretic separation of components of a sample can occur upon appropriate application of charge to electrode pair 16a and 16b. The amount of charge can be any suitable charge, for example, charges conventionally used, and appropriate charges as taught by the exemplary embodiments of the present invention described herein. A sample injection channel 17 is provided between patterned wells 12 and 13 and can carry a sample to be separated into electrophoretic separation channel 19. T-injection of the sample from either of wells 12 or 13 can be controlled by appropriate charge application to electrode pair 16c and 16d.

A sealing cover 18 can be used during operation of the device when the bubble-free electrodes of the present invention are used because no bubbles develop. Because the system can be a closed system during operation, no siphoning is required and evaporation can be eliminated or reduced. The device 11 can be loaded and then sealed, as shown, or provided with one or more access ports through the sealing cover 18. Access ports can be provided, for example, above or otherwise adjacent any number of the patterned wells 12, 13, 14, and 15.

Figure 3:
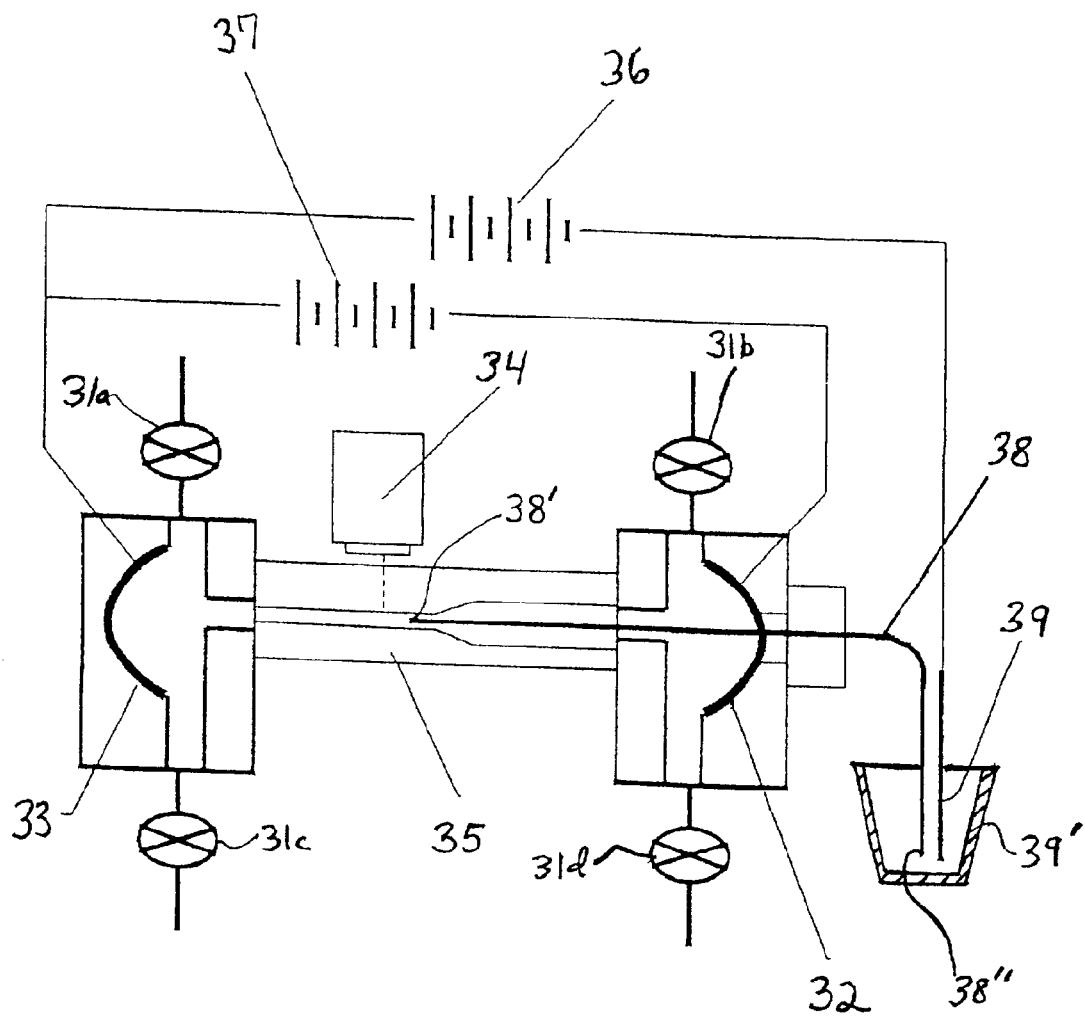
FIG. 3 is a schematic view of an analytical device according to another embodiment of the present invention.

In yet another embodiment of this invention, a system is configured as depicted in FIG. 3. In this embodiment, a technique known as "electroflow" as described in U.S. Pat. No. 5,833,826, is enabled. The system has four valves 31a–31d and palladium electrodes 32 and 33. An electric field is established within capillary tube 38 by electrodes 39 and 33. Components separated in capillary tube 38 exit the tube at end 38' and are further carried past a detection area in an electric field formed between the electrodes 32 and 33. In the embodiment shown, electrode 33 operates as an anode under normal electrolytic operating conditions.

The palladium electrodes 32 and 33 cause ions exiting the capillary tube 38 to flow in a field consistent with the field in the capillary tube 38. The present invention allows the electroflow electrodes 32 and 33 to be positioned very close to the detection cuvette 35. Thus, power supplies 36 and 37 can operate at lower voltages and still provide a field equal to that in the capillary tube 38 in the area viewed by a detector system. The detector system can include an excitation laser (not shown) and a camera 34 for imaging and color separation. This configuration also provides a substantial advantage over previous designs in that no current has to pass through any of valves 31a–31d, and no voltage must pass through reagent contained in the valve orifice. This closed system avoids siphoning from reservoir to reservoir or from load bar to reservoir.

The load bar 39 can be an array of recesses machined into a conductive, metal bar, electrode, for example, a platinum or stainless steel bar. The ends of separation capillaries can be placed in the recesses along with sample, buffer, or both. An appropriate sample injection technique can be incorporated into the system or sample reservoir 39' of load bar 39 can be drawn into end 38" of capillary tube 38.

Figure 4:
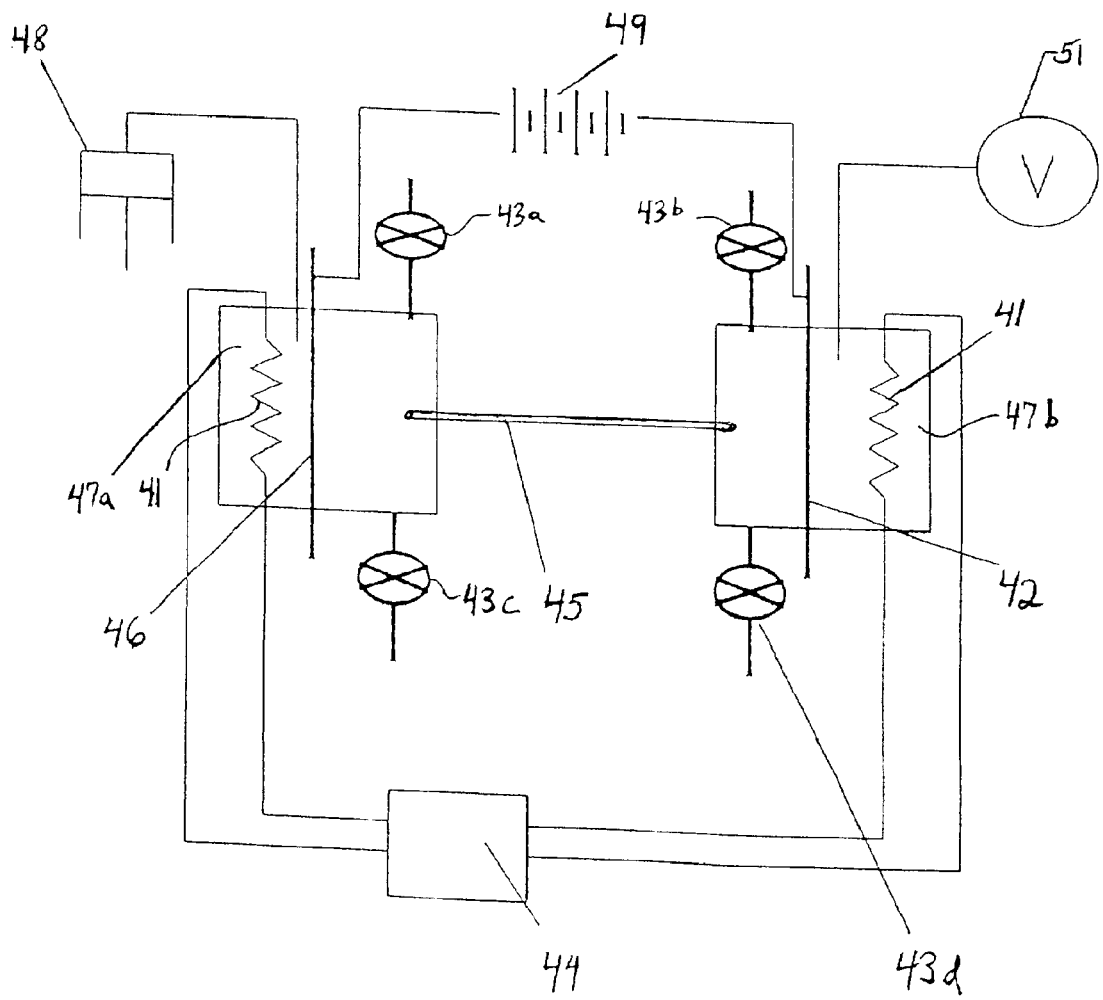
FIG. 4 is a schematic view of an analytical device according to yet another embodiment of the present invention.

Another embodiment of this invention is exemplified in FIG. 4. In this configuration, heaters 41, controlled by heater controller 44, raise the temperature of the palladium electrodes 42 and 46 to increase the hydrogen permeability of the palladium. Two reservoirs 47a and 47b are filled with a suitable conductive buffer through valves 43a–43d. A capillary 45 is filled with the same or a different conductive buffer. Each reservoir 47a and 47b has a wet-side communication with its respective valves and capillary 45, and a dry side opposite the respective electrodes 46 and 42. Hydrogen not absorbed by negative electrode 42 permeates the negative electrode 42 and forms hydrogen gas that is drawn away by a low pressure source or vacuum 51. A power supply 49 is provided. Hydrogen gas is supplied by pump 48 to the positive electrode 46 through the dry side of reservoir 47a where it permeates the electrode 46 and is believed to become oxidized such that it prevents the generation of oxygen bubbles. The principal advantage of this configuration is that there is no service cycle required to preliminarily charge the positive electrode with atomic hydrogen. Such a configuration can run continuously.

An appropriate sample injection feature can be incorporated into the system. Depending upon factors including the charges of components sought to be separated from a sample, sample injection can be configured at or near an appropriate end of capillary tube 45.

Figure 5:
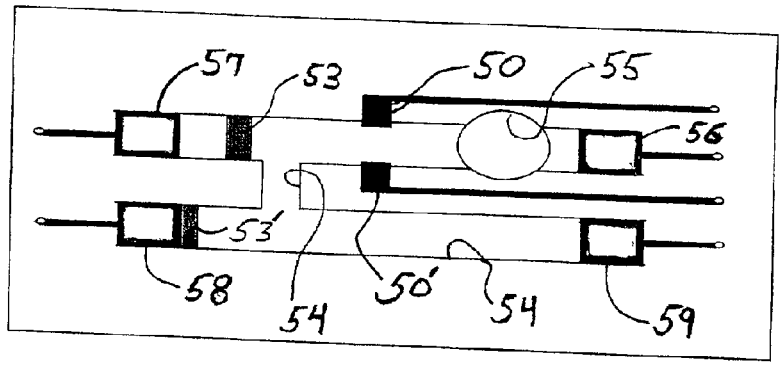
FIG. 5 is a top view of a card-type device according to an exemplary embodiment of the present invention.

FIG. 5 is a top view of a card type or card style device according to an exemplary embodiment of the present invention. The device can be microfabricated to a size as small as one mm long, or shorter. Alternatively, the device can be longer than 1 mm, such as 10 cm or longer. The device includes a channel system 54, electrode pair 50 and 50', and electrodes 56, 57, 58, and 59. All the electrodes 50, 50', 56, 57, 58, and 59 can be bubble-free electrodes according to one or more embodiments of the present invention. A sample can be loaded by injection or other contact with the device at sample access hole 55. The sample can be pre-loaded, followed by an optional sealing of the device, or provided with an opening for contacting a sample. Sealing the device can be accomplished using conventional methods, such as hermetic sealing.

Either or both electrodes of electrode pair 50 and 50' can be used to concentrate an analyte flowing in an electrophoretic field between electrodes 56 and 57. AC voltage can be applied to electrode pair 50 and 50' to cause bubble-free flow effects that can advantageously be used to influence the flow and separation of sample components. By using the different electrode pairs, different parameters of separation can be achieved, particularly when electrode pair 50 and 50' are supplied with AC voltage. The result is a tunable system that can be tuned to capture one or more very specific components or biomolecules from a sample. A further description of some uses of electrode pair 50 and 50' will be apparent to those of skill in the art when taken in conjunction with the description of FIG. 8 set forth below.

FIG. 5 also illustrates exemplary filters 53 and 53' and filter locations. Filters 53 and 53' can include porous membranes, plastic filters, gels, semipermeable membranes, anionic membranes, or other suitable separation devices that preferably can physically separate or isolate one or more components of a sample, and combinations thereof. The positioning of filter 53 allows components to pass through the filter. Components of a sample can be concentrated on or in filter 53'.

Figure 6:
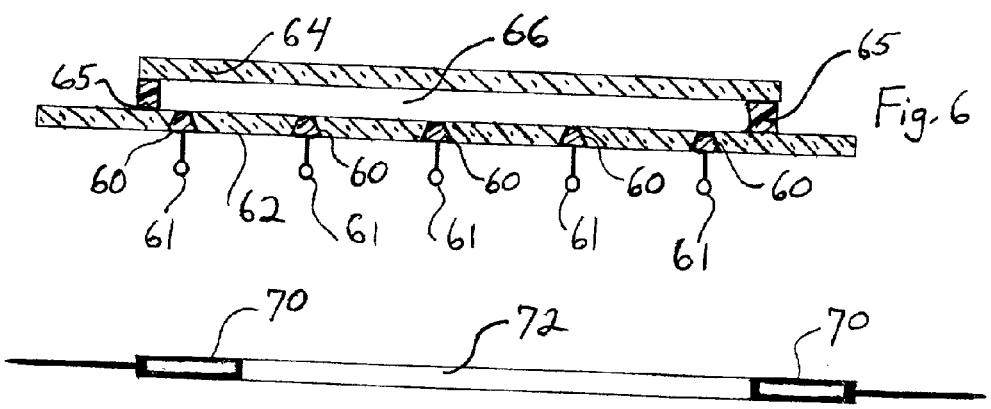
FIG. 6 is a side view of a matrix device according to an exemplary embodiment of the present invention.

FIG. 6 is a side view of a matrix device according to an exemplary embodiment of the present invention wherein reference numeral 64 depicts a cover plate or upper plate including access holes (not shown) and which is spaced from a substrate 62 which can be made, for example, of a glass or plastic material. Holes provided in substrate 62 are filled with a plurality of preferably bubble-free electrodes 60 according to the present invention. The holes in the substrate can be filled with an electrode paste material, by deposition such as electrodeposition, or plug-type electrodes can be inserted into the holes as by pressing, pouring or melt forming of the electrode material.

The cover plate 64 and the substrate 62 are spaced from each other by way of spacers 65, that can be made, for example, of an elastomeric and/or adhesive material. The spacer material can be inert in and to reagents, samples, and conditions used for an analytical technique employing the device. The space between the cover plate 64 and the substrate 62 defines a sample containment volume 66 that can be sealed when bubble-free electrodes according to the present invention are used for the electrodes 60.

Each electrode 60 is provided with a lead or connector 61 for connection to a power source. Each electrode 60 can be powered by a separate or independent power source or supply relative to the other electrodes 60, and the voltages to be applied to each electrode may differ to cause differential attraction and repulsion of analytes. Different voltages can be applied to the various electrodes at predetermined times for predetermined time periods for the purpose of moving, separating, and or concentrating sample components, such as biomolecules from a biological sample, to, from, at, or near specific ones of the electrodes. By reversing the charge applied to one or more specific electrodes, an opposite affinity for specific components can be achieved. For example, by applying an opposite charge, a biomolecule that would be attracted to a specific electrode under positive charge conditions would be repulsed by the electrode under negative charge conditions. As such, desired manipulations of biomolecules can be achieved. This embodiment of the present invention can particularly advantageously be used in the microchip matrix devices described in U.S. Pat. No. 6,071,394. Devices according to the present invention can have as many as 100 electrodes or more in a microfabricated arrangement.

Means such as a control unit can be provided to supply each electrode 60 with an independent power or voltage such that each electrode will provide different affinities to specific sample components than provided by the other electrodes. By changing the voltages applied to the various electrodes 60, by providing different voltages to each electrode, and/or by applying voltages to the electrodes for specified or sufficient time periods, selective attraction and/ or repulsion of specific sample components can be achieved. Furthermore, isolation and concentration of specific sample components can be achieved based on known or tested affinities or repulsions of such components to specific voltages. A more specific use of such a matrix device is shown in FIGS. 14a and 14b of the appended drawings, which are described in more detail below.

Figure 7A:
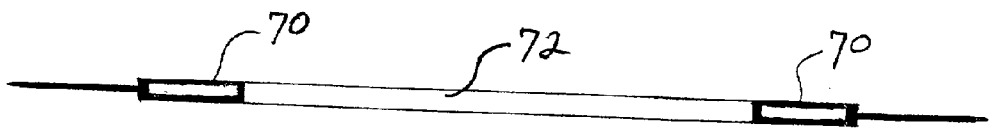
FIG. 7a is a side view of a closed capillary tube analytical device according to an exemplary embodiment of the present invention.

FIG. 7a is a side view of closed capillary tube analytical device according to an exemplary embodiment of the present invention. The device includes two bubble-free electrodes 70 spaced apart at opposite ends of a closed capillary tube 72 and provided with electrode leads or connectors. The device illustrates a use of the bubble-free electrodes of the present invention in a capillary environment. The device can be used by supplying various voltages or alternating voltages to the two electrodes, and can separate, move, concentrate, or otherwise manipulate a sample or components of a sample disposed in the capillary. After a sample is loaded into the capillary, as, for instance, by capillary action before the electrodes are placed in or on the capillary ends, the device can then be sealed by inserting or forming one or both of the electrodes in the end or ends of the capillary. Because the electrodes are bubble-free electrodes according to the present invention, the device can be permanently sealed after the electrodes are placed or formed at the capillary ends. An electrode paste material, electrode plug, or melt-molded electrode material, for example, can be used.

Figure 7B:
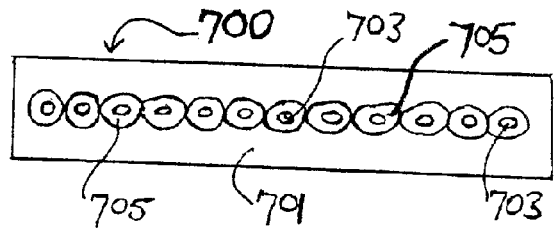

According to embodiments of the present invention wherein a plurality of such capillary devices can be arranged in an array or structure 700 as shown in FIG. 7b, a substrate 701 having a plurality of end-sealing electrodes 703 can be provided with each of the plurality of electrodes 703 being centered in a capillary receiving recess 705 formed in the substrate 701. The electrodes can be mounted or otherwise fixed or positioned on the substrate such that by aligning the capillary ends or guiding them with the capillary receiving recesses 701 formed in the substrate 701, the plurality of capillaries can be sealed and a plurality of sealed capillary devices according to the present invention can be formed simultaneously. For this use, pin-type or pin-shaped electrodes are suitable and can be sealed, adhered, melted, crimped, or otherwise fixed in place in the capillary ends after insertion or disposal of samples in the capillaries.

FIG. 8a is a side view of a concentrator device that can be used, for example, in the device of FIG. 5 wherein electrodes 73 and 74 of FIG. 8a could be used as electrodes 50 and 50' of FIG. 5. In FIG. 8a, opposing electrodes 73 and 74 are disposed on opposite sides of a channel 71. Channel 71 is defined, for example, by a tubular member. According to an embodiment of the present invention, alternating current (AC) can be applied to the opposing electrodes 73 and 74 to create a field between them that affects flow through the channel 71. As shown in FIG. 8a, trace 800 is the trace of molecules that are relatively slower moving or slower responding in the electric field formed between electrodes 73 and 74, i.e., 800 is the trace for molecules having a low charge to size ratio. Trace 802 is the trace of molecules that are relatively faster moving or faster responding in the electric field formed between electrodes 73 and 74, i.e., 802 is the trace for molecules having a high charge to size ratio. By applying even low AC voltage between electrodes 73 and 74, manipulation of charged biomolecules can be achieved as explained further below.

As shown in FIG. 8a, the hydrodynamic flow 75 of a flow through channel 71 is depicted. The hydrodynamic flow 75 is the profile of the effective velocity or the "envelope" of the flow. The hydrodynamic flow 75 has various vector components as illustrated by vectors 76a–76c. As shown in FIG. 8a, the vector or flow in the center of the channel 71, represented as vector 76c, is faster than the flow at the edges of the channel 71 represented by vectors 76a and 76b, i.e., closer to the walls of the channel-defining tubular member, hence, the longer vector length for vector 76c. This phenomenon is referred to herein as pressure driven flow.

If a specific biomolecule moves slower in an electric field, it is more often moving in the faster moving vector of the fluid flow, i.e., closer to the center of the channel than the sides. If a specific biomolecule moves faster in an electric field, it is more often moving in the slower moving vector of the fluid flow, i.e., closer to the sides of the channel than the center of the channel. As is depicted in FIG. 8a, the device of the present invention is tunable such that the frequency of specific biomolecules flowing through channel 71 can be changed or adjusted to selectively concentrate certain components of a sample flowing through the channel 71. In so doing, positioning of certain biomolecules or steering certain molecules into relatively faster or slower vectors of the fluid flow can be achieved.

According to an embodiment of the present invention, DC voltage can be supplied to electrodes at opposite ends of the tubular member-defining channel 71, to cause electrophoretic separation of a sample flowing through the channel. In the absence of a gel or sieving medium, all charged components of the sample should flow through the channel, for example, in the direction shown by the arrowheads on the traces 800 and 802. However, if AC voltage is applied to opposing electrodes such as electrodes 56 and 57 shown in FIG. 5 to form an electrophoretic separation channel, some components of the sample moving between those electrodes will move faster between the opposing electrodes 56 and 57, than others. Faster moving components such as faster moving biomolecules can become attracted to the AC field electrodes (e.g., 50 and 50' in FIG. 5 or 73 and 74 in FIG. 8a), and under certain conditions these faster moving components can become captured by the AC field electrodes. Furthermore, in devices wherein a sieving medium is provided in an electrophoretic separation channel, the additional use of AC field-generating electrodes can provide a comprehensive device having multiple dimensions of separation.

Channel sizes for the device of FIG. 8a can vary depending upon the intended use and size of the device. The channels can vary from about 1 micron to about 10 microns in width, for example. The distance between the AC field-generating electrodes 73 and 74 can vary to be any suitable distance but can be from about 2 microns to many cm. Suitable voltages to be applied to the AC field-generating electrodes 73 and 74 can be from about 1000 volts/cm to about 10,000 volts/cm, for example. The frequency of the alternating current can be from about 0.1 Hz to about 1 kHz, for example, from about 0.1 Hz to about 10 Hz. With higher voltages, lower frequencies can be used. An exemplary voltage supply scheme entails supplying +/−5 volts to electrodes 73 and 74 at a frequency of about 1 Hz with a separation distance between the electrodes of about 50 μm (micrometers).

The device of FIG. 8a, preferably when used in a device such as that of FIG. 5, can be tunable to achieve specific and effective separation of charged biomolecules and can be used to capture only specific biomolecules of a sample. The device combines the separation attributes of fluid flow or pressure driven flow separation with AC field separation effects.

Figure 8B:
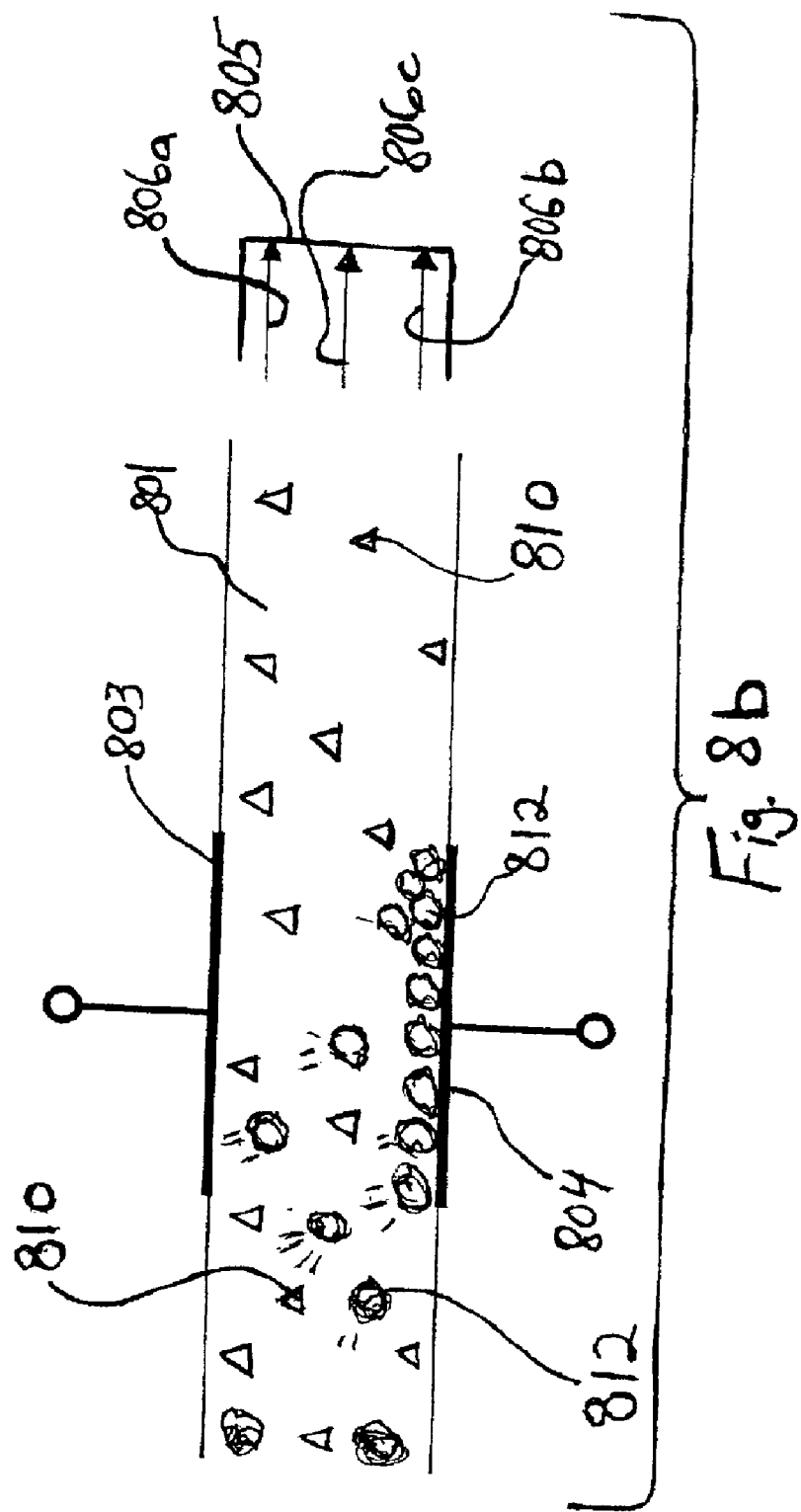
FIG. 8b is a side view of a component concentrator that uses an electrophoretic flow profile and component retaining electrodes disposed transversely with respect to the direction of electrophoretic flow.

FIG. 8b is a side view of a component concentrator that uses an electrophoretic flow profile and component-retaining electrodes disposed transversely with respect to the direction of electroosmotic or electroendoosmotic flow. As shown in FIG. 8b, the electroendoosmotic flow 805 of a flow through channel 801 is depicted. The electroendoosmotic flow 805 is the profile of the effective velocity or the "envelope" of the flow. The electroendoosmotic flow 805 has various vector components as illustrated by vectors 806a–806c, however, unlike the differing vectors on the pressure driven flow depicted in FIG. 8a, the various vectors 806a–806c are equivalent under electroendoosmotic flow conditions as depicted in FIG. 8b. As shown in FIG. 8b, the vector or flow in the center of the channel 801, represented as vector 806c, is equivalent to the flow at the edges of the channel 801 represented by vectors 806a and 806b, i.e., closer to the walls of the channel-defining tubular member.

Electrodes 803 and 804 are placed opposing one another in a direction transverse to the electroendoosmotic flow through the channel 801. If specific biomolecules 812 are charged and current is applied to electrodes 803 and 804, the field resulting between opposing electrodes 803 and 804 will cause the biomolecules 812 to be drawn-to, held, and concentrated at least one of the electrodes, electrode 804 in the embodiment shown. Non-charged components 810 will pass through channel 801 while a charged component of interest can accumulate on an appropriate electrode, 803 or 804.

As is depicted in FIG. 8b, the device of the present invention is tunable such that the frequency of specific biomolecules flowing through channel 801 can be changed or adjusted to selectively concentrate certain components of a sample flowing through the channel 801. In so doing, accumulating or concentrating certain biomolecules at electrodes 803 and 804 in the channel can be achieved.

According to an embodiment of the present invention, DC voltage can be supplied to electrodes at opposite ends of the tubular member-defining channel 801, to cause electrophoretic separation of a sample flowing through the channel. In the absence of a gel or sieving medium, all charged components of the sample should flow through the channel at equal rates. However, if AC voltage is applied to opposing electrodes such as electrodes 56 and 57 shown in FIG. 5 to form an electrophoretic separation channel, some components of the sample moving between those electrodes will move faster between the electrodes than others. Faster moving components, such as faster moving biomolecules, can become attracted to the AC field electrodes (e.g., 50 and 50' in FIG. 5 or 803 and 804 in FIG. 8*b*), and under certain conditions these faster moving components can become captured by the AC field electrodes. Furthermore, in devices wherein a sieving medium is provided in an electrophoretic separation channel, the additional use of AC field-generating electrodes can provide a comprehensive device having multiple dimensions of separation.

Channel sizes for the device of FIG. 8*b* can vary depending upon the intended use and size of the device. The channels can vary from about 1 micron to about 10 microns in width, for example. The distance between the AC field-generating electrodes 803 and 804 can vary to be any suitable distance but can be from about 2 microns to many cm. Suitable voltages to be applied to the AC field-generating electrodes 803 and 804 can be from about 1000 volts/cm to about 10,000 volts/cm, for example. The frequency of the alternating current can be from about 0.1 Hz to about 1 kHz, for example, from about 0.1 Hz to about 10 Hz. With higher voltages, lower frequencies can be used. An exemplary voltage supply scheme entails supplying +/−5 volts to electrodes 803 and 804 at a frequency of about 1 Hz with a separation distance between the electrodes of about 50 $\mu$m (micrometers).

The device of FIG. 8*b*, preferably when used in a device such as that of FIG. 5, can be tunable to achieve specific and effective separation of charged biomolecules and can be used to capture only specific biomolecules of a sample. The device combines the separation attributes of fluid flow or pressure driven flow separation with AC field separation effects.

Figure 9:
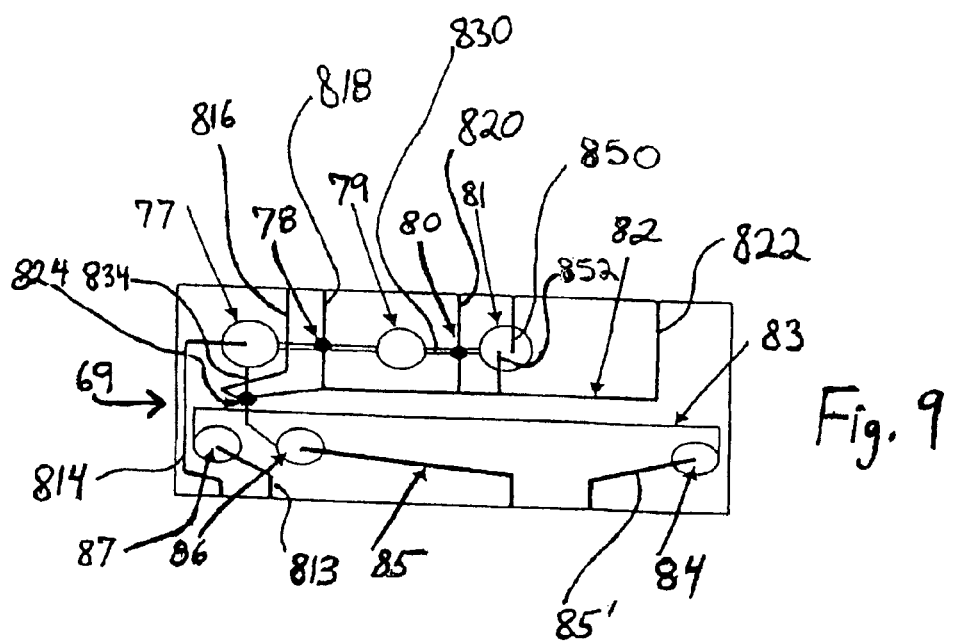
FIG. 9 is a top view of an analytical device including a pressure generator and frangible seals according to yet another embodiment of the present invention.

FIG. 9 is a top view of an analytical device 69 according to yet another embodiment of the present invention. The device includes a PCR reaction and sample chamber 77, seals 78, 80, and 824, a reagent container 79, a pressure generator 81, a low voltage conduit 82, a channel for electrophoretic separation 83, buffer containers 84, 86, and 87, low voltage conduits 85, 813, 814, 816, 818, 820, and 822, and a high voltage conduit 85', The pressure generator 81 generates pressure, as for example, by including at least one gas-generating electrode 850, 852 and conditions that enable gas generation. An exemplary system would be a gas-generating palladium electrode that has not been pre-charged according to the present invention, and run under conditions as an anode, generating oxygen gas. Other gas-generating electrode systems could be employed, including platinum electrodes, other gas-generating metals, other conducting gas-generating materials, semiconductors, and the like. The container portion of pressure generator 81 can also include appropriate buffer or other material needed to cause gas-generation, such as an ionic solution. Other generated gases can similarly be used to cause sample injection, such as hydrogen gas, chlorine gas, carbon dioxide gas, and the like.

The generation of gas by the pressure generator can be timed with the activation of current to lead or low voltage conduit 820. Application of current to conduit 820 is useful for breaking the seal 80 that is made of a frangible material, for example, a heat-meltable material. The seal 80, as well as seals 78 and 824, can include, for example, a paraffin wax material, polyethylene, polypropylene, styrene, plexiglass, or any suitable meltable plastic material or thermoplastic material. The seal can be made integral with the material of chip 69 such as formed as part of the channel 830 in the case of seals 78 and 80. Upon melting of seals 80 and 78 by application of current to conduits 818 and 820, respectively, pressure generated from pressure generator 81 can flow through channel 830, forcing reagent from reagent container 79 to flow further down channel 830 past broken or melted seal 78 and cause sample from sample container 77 to be forced through channel 834. Upon application of current through conduit 816 to melt seal 824, the sample can be T-injected into channel 83 for electrophoretic separation therein. Sample flowing from container 77 continues to buffer container 86 which can be vented (not shown). Buffer containers 84 and 87, at opposite ends of electrophoretic channel 83, can be vented but may not need vents if bubble-free electrodes according to embodiments of the present invention are employed. Conduit 85' can be the only high voltage conduit.

Conduits 816, 818, and 820 can be very narrow or made of highly resistive material and sufficiently charged to locally heat the respective seals and cause them to melt, or to cause opening of valve-type re-closable seals. An appropriate power supply for the low voltage conduits would be a supply capable of providing from about 1.5 to about 30 volts, for example, from about 5 to about 12 volts or from about 5 to about 6 volts. The high-voltage supply can supply from about 100 to about 10,000 volts, for example, from about 1000 to about 3000 volts.

The device shown in FIG. 9 is an exemplary microchip-type device that can be used to inject extremely small amount of sample into a separation channel, and the device can inject extremely small and precise amounts of appropriate reagents and sample as are required when working with nanoliter-sized volumes. The device can be microfabricated and can be made to be 10 mm long or shorter with appropriate lower voltage use, or as large as 10 cm long or longer. The device can be filled with appropriate reagents and buffers before sealing. Sample can be introduced before sealing, or the device can be provided with a sample injection port at container 77. The channels can be etched or molded or punched, and the seals can be inserted, deposited or otherwise formed in place. The substrate for the chip can be made of a glass or plastic material, or the like. The voltage conduits can be laid, welded, electrodeposited, or otherwise deposited.

FIGS. 10–13 are top views of various exemplary analytical devices according to embodiments of the present invention that benefit from the bubble-free electrodes of the present invention. In FIGS. 10–13, Ni(OH)$_x$ electrodes 89 are employed adjacent or within channels 88 and access ports 90 are provided for the channels. FIG. 10 depicts a simple, high voltage bubble-free chip device. FIG. 11 depicts a device that employs the separation technique described with respect to FIG. 8. FIG. 12 depicts an exemplary T-injection device for liquid handling wherein sample injection is immediately adjacent an electrode at an end of an electrophoretic separation channel. FIG. 13 depicts an alternative to the FIG. 12 embodiment wherein a large sample access port is provided such that no filling vent is required in the device. Sample is electrophoretically transferred through sample injection channel 88' until it reaches and is injected into separation channel 88. In each of the devices of FIGS. 10–13, appropriate leads or electrical connectors are provided for each electrode. In the devices shown in FIGS. 10–12, either access port 90 can be used as a vent for filling sample into the other access port 90.

FIGS. 14*a* and 14*b* are a side view and top view, respectively, of an analytical device according to yet another embodiment of the present invention similar to the embodiment shown in FIG. 6. In FIGS. 14*a* and 14*b*, array-like devices with Ni(OH)$_x$ electrodes are provided. The electrodes 95 are formed on or in a substrate 93 and wires 96 are connected to respective electrodes with silver paste 94. A gasket 92 separates a cover glass 91 from the electrodes 95. Access holes 90 are provided in the cover glass 91. An exemplary length 97 of such a device could be about 2 cm.

Figure 15A:
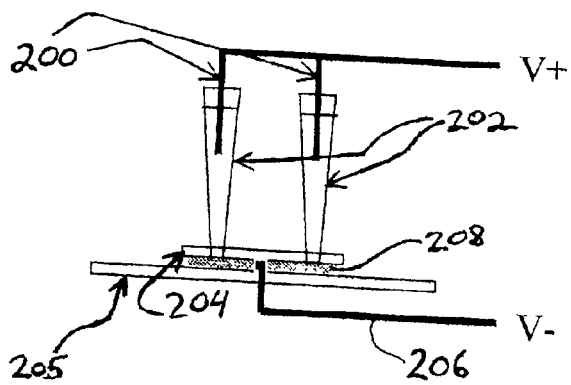
FIGS. 15a, 15b, and 16 depict various systems used in connection with the Examples described below.
Figure 15B:
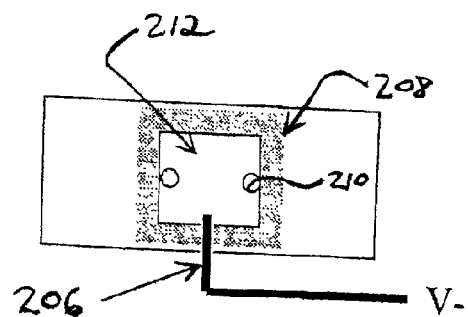
Figure 16:
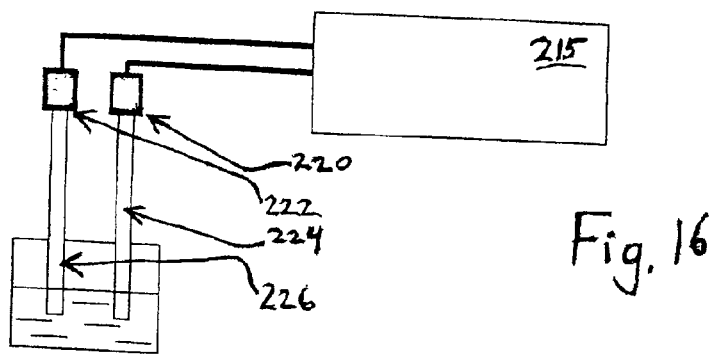

FIGS. 15a, 15b, and 16 depict various systems used to test the bubble-free and gas-generating electrodes of, and used in connection with, present invention. In FIG. 15a, in connection with the Examples described below.

EXAMPLES

Bulk Porous Electrode Experiment

A device as shown in FIGS. 15a and 15b was used in this experiment to allow large volumes of generated oxygen to be released to the atmosphere. The device is a practical device useful for testing the capacitance of palladium electrodes to last without generating bubbles. The device can compare palladium electrodes to platinum electrodes. FIG. 15a is a side view of the testing device and FIG. 15b is a bottom view of the same device. The device includes platinum wires 200, pipette tips 202 open at their upper ends, microscopic slides 204 and 205, a porous palladium electrode 206, a rubber gasket 208, access holes 210 in slide 204, and a buffer 212. The cell containing the electrode had dimensions of 15×15×1 mm. Two access holes were drilled in the upper glass for connecting the cell to two pipette tips with platinum wires connected in parallel and serving as the opposite electrode. The tested electrode was made from nanoporous palladium, grain size 30 nm, specific density 5.424 g/cm$^3$ (45% Pd), size 1×1.5×8 mm. At the start, all reservoirs or containers were filled with the same buffer material. The Pd electrode was immersed in the buffer 1.5 mm deep. The volume of Pd exposed to the buffer was 2.25 mm$^3$. Using Faraday's law, as is known to those skilled in the art, the amount of gas generated by the platinum electrode and absorbed by the palladium electrode of the present invention can be calculated.

Fresh Electrode Run:

A buffer comprising 10 mM Tris HCl mixed with 1 mM EDTA was used and had a pH of about 8.0. The applied power was a voltage of 100V, an initial current of 3 mA, and a final current of 0.5 mA. No bubbles formed for 50 minutes, and the total charge that passed was about 5C (equivalent to 0.55 ml of H$_2$). The polarity was then reversed, and the cell was run at an initial current of 0.5 mA, and a final current of 0.9 mA, whereby no O$_2$ bubbles formed for 35 minutes.

Repeated Runs:

A buffer was provided and comprised a H$_2$SO$_4$ 1:100 dilution. A current of 4 mA was applied and the anode ran bubble-free for 5 minutes. With an applied current of 2.3 mA, the anode ran bubble-free for 10 minutes. The charge that passed was ~1.2C (0.14 ml H$_2$).

After a few repeated runs, some cracks were observed in the part of the electrode that is exposed to the buffer because of different expansion of the immersed and non-immersed part of the electrode. The storage or diffusion of H$_2$ was negatively affected by the cracks at higher currents. Some bubbles were observed at sharp edges of the cracks before the electrode had reached full capacitance.

Thin Film Electrodes.

Thin Cu wires were soldered to one end of the electrodes. The exposed part of the wire and the solder were coated with epoxy to prevent contact with buffer. For measurements the electrodes were immersed in a buffer in a small Petri dish. The buffer included 10 mM Tris HCl mixed with 1 mM EDTA, and had a pH of about 8.0. Applied voltages, currents, and time to formation of H$_2$ were monitored.

Formation of bubbles was observed under a microscope.

Three types of electrodes were tested:
(1) thin film nanoporous Pd 20 μm thick (11×6 mm) baked at 600° C. on Al$_2$O$_3$ substrate;
(2) thin film nanoporous Pd 40 μm thick (5.5×10 mm) film dried at 100° C., on Al$_2$O$_3$ substrate; and
(3) solid palladium foil 250 μm thick used in U.S. Pat. No. 5,833,826. The foil was coated with epoxy and only one side dimensioned 14×4 mm was exposed to the buffer.

The conditions for the first electrode were as follows: applied voltage 4 V, current 1.1 mA, time to first bubbles 20 min, total charge passed 1.3 C. Reversed polarity, current 1.4 mA no O$_2$ bubbles for 15 minutes.

The conditions for the second electrode were as follows: applied voltage 20V, current 10 mA, time to first bubbles 5 min, total charge 3C.

The bubbles in both cases were formed at the edges were the electric current was strongest. For different electrode arrangement, the total charge could be higher.

The conditions for the third electrode were as follows. The applied voltage was 4V, the applied current was 1 mA, the time until first bubble formation was 100 min, and the total charge that passed was 6 C. At an applied voltage of 15V, an applied current of 11 mA, for a time period of 30 min, the total charge that passed was 19.8 C. Under reverse polarity conditions, the applied voltage was 10 V, the applied current was 6.2 mA, and the time period was for 12 min.

Summary of the Charges Passed for the Tested Pd Electrodes

| Material | Charge per mm$^3$ under exposed area | Exposed surface area | Total volume |
| --- | --- | --- | --- |
| nanoporous Pd bulk | 2.2 C | 9 mm$^2$ | 5.5 mm$^3$ |
| nanoporous film #1 | 1 C | 66 mm$^2$ | 1.3 mm$^3$ |
| nanoporous film #2 | 1.4 C | 55 mm$^2$ | 2.2 mm$^3$ |
| solid Pd | 1.4 C | 56 mm$^2$ | 25 mm$^3$ |

Nickel Hydroxide Electrodes

Nickel hydroxides is use in rechargeable alkaline batteries. Unlike Pd electrodes nickel hydroxides electrodes react with H$^+$ and OH$^-$ ions without generating bubbles of H$_2$ or O$_2$ according to the formulae:

$Ni(OH)_2(s) + 2OH^- \leftrightharpoons Ni(OH)_4(s) + 2e^-$ and

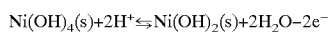

$Ni(OH)_4(s) + 2H^+ \leftrightharpoons Ni(OH)_2(s) + 2H_2O - 2e^-$ where: (s)—solid, e$^-$—electron The electrode on one side should be connected to an electronic conductor (metal) and parameters like geometry, current densities, grain size, packing density, electronic conductivity of electrodes, crack, etc. play important roles in optimizing the system. However, the relatively low currents used in electrophoresis of biomolecules works to an advantage.

Nickel Hydroxide Electrodes Experiment.

Two short glass tubes I.D. 1.5 mm, 10 mm long were packed with mixture of Ni(OH)$_2$ and Ni(OH)$_4$ from partially charged Ni—Cd battery. On one side, Pt wires were inserted 3 mm inside the mixture and the side was sealed with epoxy. The short tubes then were put on the ends of thinner glass tubes O.D 1.2 mm, I.D. 0.6 mm, 135 mm long filled with 50 mM Tris buffer and the gap between them was sealed with epoxy. The two open ends of the longer tubes were placed in a vial filled with 50 nM Tris buffer.

FIG. 16 shows a device for testing the length of time, as determined by visual inspection, before bubble formation under high voltage conditions in a nickel hydroxide electrode system. The Pt wires were connected to KEITHLEY electrometer and a high voltage potential of 1000V DC was applied, as shown in FIG. 16. In the device of FIG. 16, reference numeral 215 depicts a KEITHLEY electrometer, 220 and 222 depict electrodes, and 224 and 226 depict long tubes. The measured current equaled 275 µA. After 10 min, small bubbles on one electrode were visible. The total charge passed equaled 0.165 C, which is only a fraction of full theoretical capacity of the electrodes (~10 C). It was visible that the packing of the nickel hydroxide was poor and there was a short path to the Pt wires. To fix the problem a paste of finely pulverized nickel hydroxide is made with NAFION solution as a binder. The specific composition of the paste can be determined by the requirements of the specific application for which it is used.

In conclusion, the two selected materials for bubble-free electrodes worked as expected and together can be used to cover a wide range of applications. The palladium electrodes are more expensive but in solid or bulk nanoporous form can be incorporated in reusable devices. Nanoporous palladium ink can be applied by printing on glass or plastics. Solid or baked at higher temperature palladium electrodes have high electronic conductivity and are advantageous in high-speed applications like traveling wave separation. The connection to external electronics for the tested electrodes is relatively simple for the same reason.

Nickel hydroxide electrodes are inexpensive, can be easily manufactured, and are useful in disposable devices. The electrodes are optimized for use as cathodes or anodes.

Electroflow Example 1

Figure 17:
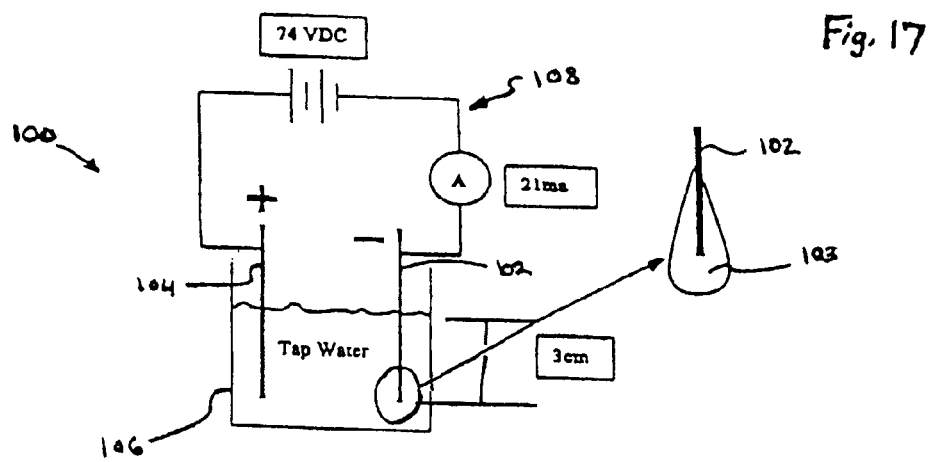
FIG. 17 is a schematic illustration of an apparatus according to an embodiment of the present invention including an enlarged portion showing a tip of an epoxy-coated electrode.

Referring now to FIG. 17, an electroflow arrangement is shown for establishing whether electrodes made of palladium would eliminate the volume of hydrogen gas that would be generated during a sequencing run on the electroflow breadboard as described in U.S. Pat. No. 5,833,826. As previously mentioned, bubbles generated from electrolysis tend to complicate the fluid path and heat management aspects of electroflow breadboards.

As seen in FIG. 17, the arrangement 100 includes negative electrode 102 and positive electrode 104 made of palladium tubing, and having outside diameters of 1 mm and 0.1 mm walls. The electrodes 102 and 104 were immersed in tap water contained in a reservoir 106. The immersion depth of the electrodes was about 3 cm. An electrical system 108 was used to supply a DC voltage of about 74 V to electrodes 102 and 104 for electrolysis and the current noted was about 21 mA. The arrangement was maintained at a temperature of approximately 21° C. The tip of electrode 102 was crimped and provided with an epoxy insulator 103. The role of the epoxy insulator was to minimize field concentrations at the edge provided by the tip of the electrode 102 and minimize localized bubble formation.

After a period of approximately 12 minutes, bubbles appeared at the negative palladium electrode. In order to remove the hydrogen from the negative electrode 102, the polarity of the electrodes was reversed for approximately the same amount of time, that is, for approximately 12 minutes. It was noted that oxygen gas did not appear at electrode 102, as a positive electrode, for approximately 12 minutes.

The above experiment was repeated three times with approximately the same results. A vacuum was applied to the negative electrode but no effect was noted.

The above experiment led to the conclusion that at the noted temperature, palladium absorbs a certain volume of hydrogen at the surface only. The current noted in the above experiment, that is, 21 mA, was higher than the usual current for electroflow applications. However, with the assumption that electrolysis times of about 60 minutes or longer will not be unusual in practice, the electroflow current corresponding to available flow cells and plumbing was calculated and verified on an experimental basis as being about 13 mA, as will be described in further detail below. Future modifications can lower the value for current to approximately 9 mA, such as a slit height of 0.008 inch. It is to be understood that the slit is a rectangular open section in the flow cell. By decreasing the height of the slit, the resistive section of the conductive polymer is decreased, resulting in an increase in the effective resistance through the section. The resistance increase lowers the current for a given voltage as given in Ohm's law.

Considering Equation 1 below:

$$N \alpha T \times I \qquad \text{Equation 1}$$

where:
N: the total number of hydrogen atoms absorbed;
T: run time of electrolysis in minutes;
I: applied current in mA,
what is expressed is that the total number of hydrogen atoms absorbed is proportional to the run time of electrolysis in minutes, times the applied current in mA. In Example 1, I was equal to 21 mA and T was equal to 12 minutes. Therefore:

$$N \alpha 12 \text{ min} \times 21 \text{ mA} \qquad \text{Equation 2}$$

As previously stated, the electroflow current corresponding to available flow cells and plumbing was calculated and verified on an experimental basis as being about 13 mA. Therefore:

$$N \alpha 19.4 \text{ min} \times 13 \text{ mA} \qquad \text{Equation 3}$$

In other words, one would have 19.4 minutes of bubble-free run time in electrolysis with an electrode of the surface area used in Electroflow Example 1. Increasing the surface area of the electrode would increase the bubble-free run time. The surface area of electrode 102 would be:

$$\begin{aligned}A &= \text{immersion depth} \times 2 \times \text{radius of electrode} \times \pi \\ &= 30 \text{ mm} \times 2 \times 0.5 \text{ mm} \times \pi = 94.24 \text{ sq. mm}\end{aligned} \qquad \text{Equation 4}$$

Thus, for an area A of about 94.24 sq.mm, at about 13 mA, the run time can go up to about 19.4 min without the appearance of hydrogen gas. Thus, for a run time of about 60 min, the area must be:

$$A=(60/19.4) \times 94.24 \text{ sq.mm}=292.175 \text{ sq.mm} \qquad \text{Equation 5}$$

In view of the above, it can be concluded that an electrode having a surface area of approximately 300 sq.mm should work in the arrangement of FIG. 17.

Figure 18:
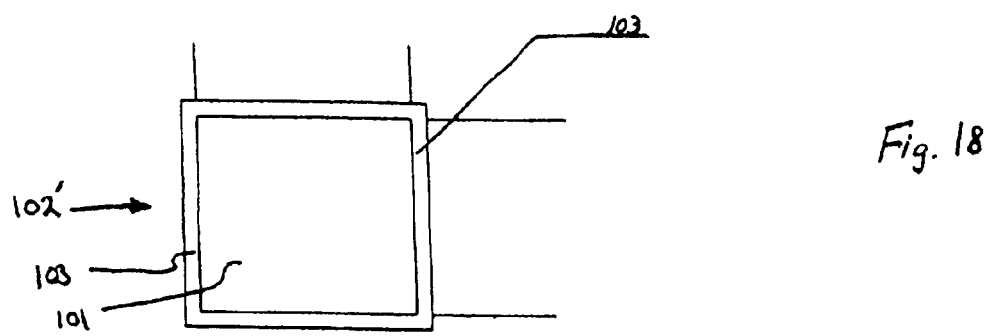
FIG. 18 is a schematic drawing illustrating a modified electrode useful in accordance with embodiments of the present invention.

Referring now to FIG. 18, a design for a modified electrode is shown in the form of electrode 102'. Here, the electrode 102' includes a sheet of palladium measuring about 12.5 mm by 12.5 mm, and having been insulated at edges thereof with an insulating border 103 bordering an exposed palladium surface 101.

According to one embodiment of the present invention, a set-up for removing the hydrogen from the palladium surface can involve a special hydrogen removal electrode located close to the palladium electrode. This hydrogen removal electrode would be used only during the "cleaning"

cycle of the electroflow arrangement. Close proximity would allow very high currents such as 1000 mA to be used at low voltages, such as 12 volts DC, over a proportionally short time, such as one minute.

According to an alternative embodiment of the present invention, the preference of oxygen to react with hydrogen can be exploited. According to this embodiment, two palladium electrodes similar to the one described in FIG. 18 can be used. Prior to using the machine for sequencing, a reverse polarity would be applied to the electrodes. This would saturate the normally positive electrode with hydrogen. During a sequencing run, the electrode would be positive, and oxygen would then react preferentially with the hydrogen saturated electrode rather than produce oxygen bubbles. The negative palladium electrode would absorb the hydrogen bubbles. At the end of the sequencing cycle, the polarity of the electrodes would again be reversed to "recharge" the electrodes prior to the next sequencing run. It is further possible to use a positive electrode having a surface area of only about one half of the surface area of the negative electrode since only one atom of oxygen is produced for every two atoms of hydrogen used. Possible benefits of the above design include a bubble-free electroflow system, a very short conductive path for electroflow resulting in substantially lower electroflow voltage, no weirs or associated valves, and potential cost savings and enhanced performance.

Electroflow Example 2

Figure 19:
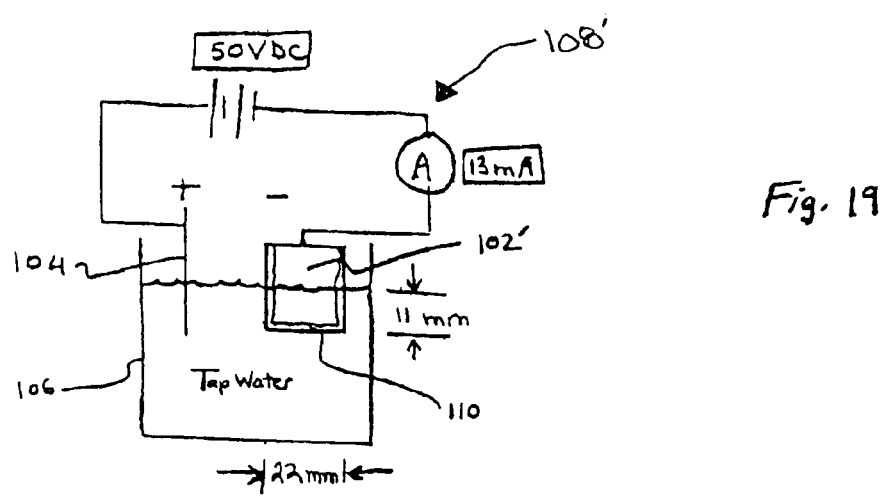
FIG. 19 is a schematic illustration of an apparatus according to yet another embodiment of the present invention.

Referring now to FIG. 19, a modified version of the arrangement of FIG. 17 was used. Here, electrode 102 of FIG. 17 was replaced with electrode 102'. Electrode 102' was a flat sheet of palladium having been placed in the tap water at an immersion depth of about 11 mm, and further having a width of about 22 mm. The capacity to absorb hydrogen being a surface phenomenon, very thin gage or material was used. The edges of electrode 102' were coated with an insulating border 110 made of epoxy in order to minimize field concentrations at the edges of the electrode. An electrical system 108 ' was used to supply a DC voltage of about 50 V to electrodes 102' and 104 for electrolysis and the current noted was about 13 mA.

After a period of approximately 60 minutes, bubbles appeared at the negative palladium electrode. In order to remove the hydrogen from the negative electrode 102', the polarity of the electrodes was reversed for approximately the same amount of time, that is, for approximately 60 minutes. It was noted that oxygen gas did not appear at electrode 102', acting as a positive electrode for the duration of the run.

Figure 20:
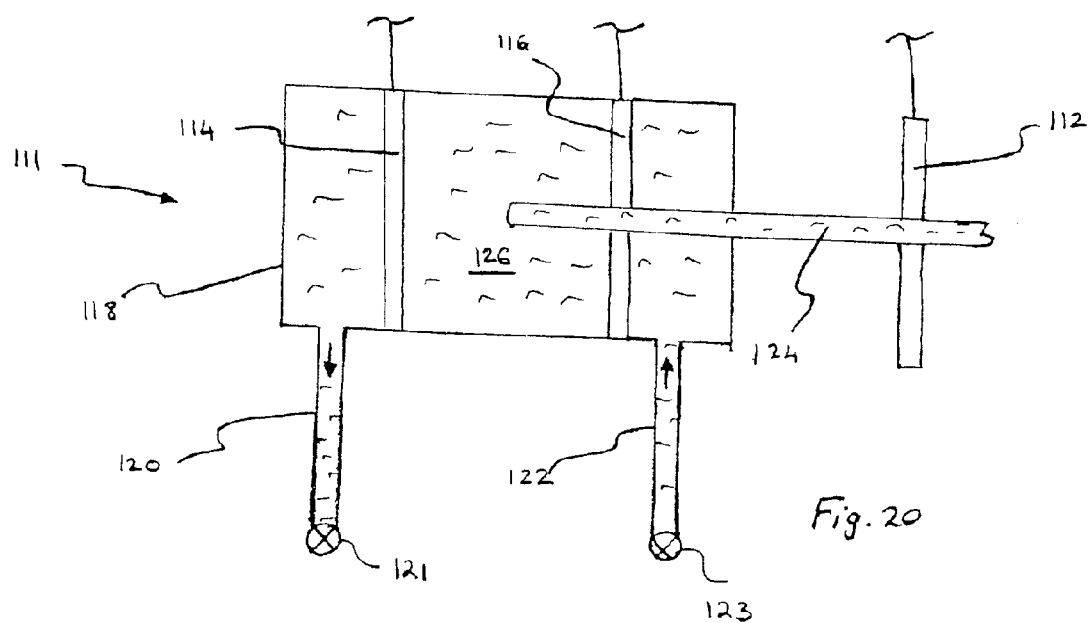
FIG. 20 is a schematic illustration of an electrophoretic device according to an embodiment of the present invention.

According to one embodiment of the present invention, the principles demonstrated in Examples 1 and 2 can be put into practice. In this regard, reference is now made to FIG. 20, where an electrophoretic arrangement 111 according to an embodiment of the present invention is depicted in schematic form. Here, a first electrode 112, a second electrode 114, and a third electrode 116, all made of palladium, are shown used in conjunction with an array of channels, such as, for example, capillaries as shown at 124. The second electrode 114 and third electrode 116 are placed in a cuvette 118 supplied with an electrolyte such as a polymer, for example such as POP6 electrolyte or another suitable and/or conventional electrolyte. The electrolyte was supplied through an inlet 122 and the polymer was capable of being discharged through an outlet 120 as shown. The inlet 122 and outlet 120 were provided with respective valves 123 and 121 for controlling the flow of polymer into and out of the cuvette 118.

In operation, cuvette 118 was first filled with an electrolytic polymer, and valves 121 and 123 were then closed. Then, the third electrode 116 was set to be an anode, and the second electrode 114 was set to be a cathode. The electrolysis was then run for a period of time to charge the second electrode 114 to the extent desired. The period of time of this first run corresponded approximately to the period of time that the sequencing run was subsequently performed without generating bubbles at the electrodes. During this first run, oxygen bubbles formed at the second electrode 114. Thereafter, the cuvette polymer was washed out with fresh polymer, and, after a sample injection, the first electrode 112 was set to be a cathode, the second electrode 114 was set to be an anode, and the third electrode 116 was set to be a cathode. An electrophoresis run was then advantageously made without the formation of bubbles at the second electrode, for the reasons described in relation to Electroflow Examples 1 and 2 above. In this way, a disruption of the electrophoresis by bubbles was advantageously prevented.

The above Electroflow Examples according to the present invention represent uses of the principles of the present invention in an electrophoretic system similar to the system shown in U.S. Pat. No. 5,833,826, the disclosure of which is incorporated herein in its entirety by reference.

Comparative Examples Using Stainless Steel Electrodes

According to other Experiments, it has been found that, while the use of stainless steel electrodes leads, after a very short time, to the formation of gas bubbles at those electrodes under conditions of electrolysis, the use of electrodes made of palladium, on the other hand, prevents the formation of such gas bubbles for a much longer period of time. It is noted that the period of time during which a palladium electrode absorbs hydrogen atoms during electrolysis is, among other things, dependent on its exposed surface area, that is, the surface area available for electrolysis. The larger the exposed surface area of the electrode, the longer the period of time during which the palladium electrode will prevent the formation of gas bubbles under conditions of electrolysis. Stainless steel electrodes, on the other hand, lead to gas bubble formation in as short a time as 15 seconds.

It will be apparent to those skilled in the art that various modifications and variations can be made to the embodiments of the present invention without departing from the spirit or scope of the present invention. Thus, it is intended that the present invention cover other modifications and variations of this invention within the scope of the appended claims and their equivalents.

What is claimed is:

1. An analytical device comprising an electrochemical cell and a sample containment device,
    said electrochemical cell comprising:
        an anodic reservoir adapted to receive an electrolyte;
        a cathodic reservoir adapted to receive an electrolyte;
        a connection between said anodic reservoir and said cathodic reservoir for permitting communication of electrolyte from at least one of said reservoirs to the other of said reservoirs;
        a first bubble-free electrode having been precharged as a cathode to have hydrogen absorbed therein, and the bubble-free electrode being disposed within one of said anodic reservoir and said cathodic reservoir;
        a second electrode disposed within the other of said anodic reservoir and said cathodic reservoir;
        a power source having a positive terminal in electrical contact with said first electrode, and a negative terminal in electrical contact with said second electrode, said electrochemical cell operating in an electrolytic mode and generating an electrical field when said power source is turned on; and
a power source polarity inverting device for switching the contacts between the terminals of said power source and said first and second electrodes such that said negative terminal is in electrical contact with said first electrode and said positive terminal is in electrical contact with said second electrode; and
said sample containment device comprising a sample containment chamber, said sample containment chamber including an opening for introducing a sample into said chamber and being positioned with respect to said electrochemical cell such that an electrical field generated by said electrochemical cell can influence at least one property of at least one component of a sample disposed in said sample containment chamber;
wherein at least one of said first and second electrodes comprises a nickel hydroxide material.

2. The analytical device of claim 1, wherein said nickel hydroxide material includes a nickel hydroxide compound of the formula $Ni(OH)_x$ wherein x is 2 or 4.

3. An analytical device comprising an electrochemical cell and a sample containment device,
said electrochemical cell comprising:
an anodic reservoir adapted to receive an electrolyte;
a cathodic reservoir adapted to receive an electrolyte;
a connection between said anodic reservoir and said cathodic reservoir for permitting communication of electrolyte from at least one of said reservoirs to the other of said reservoirs;
a first bubble-free electrode having been precharged as a cathode to have hydrogen absorbed therein, and the bubble-free electrode being disposed within one of said anodic reservoir and said cathodic reservoir;
a second electrode disposed within the other of said anodic reservoir and said cathodic reservoir;
a power source having a positive terminal in electrical contact with said first electrode, and a negative terminal in electrical contact with said second electrode, said electrochemical cell operating in an electrolytic mode and generating an electrical field when said power source is turned on; and
a power source polarity inverting device for switching the contacts between the terminals of said power source and said first and second electrodes such that said negative terminal is in electrical contact with said first electrode and said positive terminal is in electrical contact with said second electrode; and
said sample containment device comprising a sample containment chamber, said sample containment chamber including an opening for introducing a sample into said chamber and being positioned with respect to said electrochemical cell such that an electrical field generated by said electrochemical cell can influence at least one property of at least one component of a sample disposed in said sample containment chamber;
wherein both of said first and second electrodes comprises a nickel hydroxide material.

4. The analytical device of claim 3, wherein said nickel hydroxide material includes a nickel hydroxide compound of the formula $Ni(OH)_x$ wherein x is 2 or 4.

5. An analytical device comprising an electrochemical cell and a sample containment device,
said electrochemical cell comprising:
an anodic reservoir adapted to receive an electrolyte;
a cathodic reservoir adapted to receive an electrolyte;
a connection between said anodic reservoir and said cathodic reservoir for permitting communication of electrolyte from at least one of said reservoirs to the other of said reservoirs;
a first bubble-free electrode having been precharged as a cathode to have hydrogen absorbed therein, and the bubble-free electrode being disposed within one of said anodic reservoir and said cathodic reservoir;
a second electrode disposed within the other of said anodic reservoir and said cathodic reservoir;
a power source having a positive terminal in electrical contact with said first electrode, and a negative terminal in electrical contact with said second electrode, said electrochemical cell operating in an electrolytic mode and generating an electrical field when said power source is turned on; and
a power source polarity inverting device for switching the contacts between the terminals of said power source and said first and second electrodes such that said negative terminal is in electrical contact with said first electrode and said positive terminal is in electrical contact with said second electrode; and
said sample containment device comprising a sample containment chamber, said sample containment chamber including an opening for introducing a sample into said chamber and being positioned with respect to said electrochemical cell such that an electrical field generated by said electrochemical cell can influence at least one property of at least one component of a sample disposed in said sample containment chamber;
wherein at least one of said first and second electrodes comprises nickel-cadmium.

6. An analytical device comprising an electrochemical cell and a sample containment device,
said electrochemical cell comprising:
an anodic reservoir adapted to receive an electrolyte;
a cathodic reservoir adapted to receive an electrolyte;
a connection between said anodic reservoir and said cathodic reservoir for permitting communication of electrolyte from at least one of said reservoirs to the other of said reservoirs;
a first bubble-free electrode having been precharged as a cathode to have hydrogen absorbed therein, and the bubble-free electrode being disposed within one of said anodic reservoir and said cathodic reservoir;
a second electrode disposed within the other of said anodic reservoir and said cathodic reservoir;
a power source having a positive terminal in electrical contact with said first electrode, and a negative terminal in electrical contact with said second electrode, said electrochemical cell operating in an electrolytic mode and generating an electrical field when said power source is turned on; and
a power source polarity inverting device for switching the contacts between the terminals of said power source and said first and second electrodes such that said negative terminal is in electrical contact with said first electrode and said positive terminal is in electrical contact with said second electrode; and
said sample containment device comprising a sample containment chamber, said sample containment chamber including an opening for introducing a sample into said chamber and being positioned with respect to said electrochemical cell such that an electrical field generated by said electrochemical cell can influence at least one property of at least one component of a sample disposed in said sample containment chamber;
wherein at least one of said first and second electrodes comprises an ionic liquid.

7. An analytical device comprising an electrochemical cell and a sample containment device, said electrochemical cell comprising:
an anodic reservoir adapted to receive an electrolyte;
a cathodic reservoir adapted to receive an electrolyte;
a connection between said anodic reservoir and said cathodic reservoir for permitting communication of electrolyte from at least one of said reservoirs to the other of said reservoirs;
a first bubble-free electrode having been precharged as a cathode to have hydrogen absorbed therein, and the bubble-free electrode being disposed within one of said anodic reservoir and said cathodic reservoir;
a second electrode disposed within the other of said anodic reservoir and said cathodic reservoir;
a power source having a positive terminal in electrical contact with said first electrode, and a negative terminal in electrical contact with said second electrode, said electrochemical cell operating in an electrolytic mode and generating an electrical field when said power source is turned on; and
a power source polarity inverting device for switching the contacts between the terminals of said lower source and said first and second electrodes such that said negative terminal is in electrical contact with said first electrode and said positive terminal is in electrical contact with said second electrode; and said sample containment device comprising a sample containment chamber, said sample containment chamber including an opening for introducing a sample into said chamber and being positioned with respect to said electrochemical cell such that an electrical field generated by said electrochemical cell can influence at least one property of at least one component of a sample disposed in said sample containment chamber;

wherein at least one of said first and second electrodes comprises an ionic conductor selected from liquid electrolytes, gels, polymer electrolytes, ceramics, glasses, membranes, and combinations thereof.

8. An electrochemical cell comprising:
an anodic reservoir adapted to receive an electrolyte;
a cathodic reservoir adapted to receive an electrolyte;
an electrical connection between said anodic reservoir and said cathodic reservoir for permitting communication of electrolyte from at least one of said reservoirs to the other of said reservoirs;
a first bubble-free hydrogen absorbing electrode having been precharged as a cathode to have hydrogen absorbed therein, and the bubble-free electrode being disposed within one of said anodic reservoirs and said cathodic reservoir;
a second electrode disposed within the other of said anodic reservoir and said cathodic reservoir;
a power source having a positive terminal in electrical contact with said first electrode, and a negative terminal in electrical contact with said second electrode; and
a power source polarity inverting device for switching the contacts between the terminals of said power source and said first and second electrodes such that said negative terminal is in electrical contact with said first electrode and said positive terminal is in electrical contact with said second electrode;
wherein at least one of said first and second electrodes comprises a nickel hydroxide material.

9. The electrochemical cell of claim 8, wherein said nickel hydroxide material includes a nickel hydroxide compound of the formula $Ni(OH)_x$ wherein x is either 2 or 4.

10. An electrochemical cell comprising:
an anodic reservoir adapted to receive an electrolyte;
a cathodic reservoir adapted to receive an electrolyte;
an electrical connection between said anodic reservoir and said cathodic reservoir for permitting communication of electrolyte from at least one of said reservoirs to the other of said reservoirs;
a first bubble-free hydrogen absorbing electrode having been precharged as a cathode to have hydrogen absorbed therein, and the bubble-free electrode being disposed within one of said anodic reservoirs and said cathodic reservoir;
a second electrode disposed within the other of said anodic reservoir and said cathodic reservoir;
a power source having a positive terminal in electrical contact with said first electrode, and a negative terminal in electrical contact with said second electrode; and
a power source polarity inverting device for switching the contacts between the terminals of said power source and said first and second electrodes such that said negative terminal is in electrical contact with said first electrode and said positive terminal is in electrical contact with said second electrode;
wherein both of said first and second electrodes comprises a nickel hydroxide material.

11. The electrochemical cell of claim 10, wherein said nickel hydroxide material includes a nickel hydroxide compound of the formula $Ni(OH)_x$ wherein x is either 2 or 4.

12. An electrochemical cell comprising;
an anodic reservoir adapted to receive an electrolyte;
a cathodic reservoir adapted to receive an electrolyte;
an electrical connection between said anodic reservoir and said cathodic reservoir for permitting communication of electrolyte from at least one of said reservoirs to the other of said reservoirs;
a first bubble-free hydrogen absorbing electrode having been precharged as a cathode to have hydrogen absorbed therein, and the bubble-free electrode being disposed within one of said anodic reservoirs and said cathodic reservoir;
a second electrode disposed within the other of said anodic reservoir and said cathodic reservoir;
a power source having a positive terminal in electrical contact with said first electrode, and a negative terminal in electrical contact with said second electrode; and
a power source polarity inverting device for switching the contacts between the terminals of said power source and said first and second electrodes such that said negative terminal is in electrical contact with said first electrode and said positive terminal is in electrical contact with said second electrode;
wherein at least one of said first and second electrodes comprises nickel-cadmium.

13. An electrochemical cell comprising;
an anodic reservoir adapted to receive an electrolyte;
a cathodic reservoir adapted to receive an electrolyte;
an electrical connection between said anodic reservoir and said cathodic reservoir for permitting communication of electrolyte from at least one of said reservoirs to the other of said reservoirs;
a first bubble-free hydrogen absorbing electrode having been precharged as a cathode to have hydrogen absorbed therein, and the bubble-free electrode being disposed within one of said anodic reservoirs and said cathodic reservoir;

a second electrode disposed within the other of said anodic reservoir and said cathodic reservoir;

a power source having a positive terminal in electrical contact with said first electrode, and a negative terminal in electrical contact with said second electrode; and a power source polarity inverting device for switching the contacts between the terminals of said power source and said first and second electrodes such that said negative terminal is in electrical contact with said first electrode and said positive terminal is in electrical contact with said second electrode;

wherein at least one of said first and second electrodes comprises an ionic liquid.

14. An electrochemical cell comprising;

an anodic reservoir adapted to receive an electrolyte;

a cathodic reservoir adapted to receive an electrolyte;

an electrical connection between said anodic reservoir and said cathodic reservoir for permitting communication of electrolyte from at least one of said reservoirs to the other of said reservoirs;

a first bubble-free hydrogen absorbing electrode having been precharged as a cathode to have hydrogen absorbed therein, and the bubble-free electrode being disposed within one of said anodic reservoirs and said cathodic reservoir;

a second electrode disposed within the other of said anodic reservoir and said cathodic reservoir;

a power source having a positive terminal in electrical contact with said first electrode, and a negative terminal in electrical contact with said second electrode; and a power source polarity inverting device for switching the contacts between the terminals of said power source and said first and second electrodes such that said negative terminal is in electrical contact with said first electrode and said positive terminal is in electrical contact with said second electrode;

wherein at least one of said first and second electrodes comprises an ionic conductor selected from liquid electrolytes, gels, polymer electrolytes, ceramics, glasses, membranes, and combinations thereof.

* * * * *